US010028659B2

(12) United States Patent
Schwartz et al.

(10) Patent No.: US 10,028,659 B2
(45) Date of Patent: Jul. 24, 2018

(54) APTAMER-BASED SENSORS, IMPLANTABLE DEVICES AND DETECTION SYSTEM

(71) Applicant: Verily Life Sciences LLC, Mountain View, CA (US)

(72) Inventors: Jerrod Joseph Schwartz, Mountain View, CA (US); Jason Donald Thompson, Mountain View, CA (US); Vikram Singh Bajaj, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 396 days.

(21) Appl. No.: 14/669,424

(22) Filed: Mar. 26, 2015

(65) Prior Publication Data
US 2016/0278638 A1  Sep. 29, 2016

(51) Int. Cl.
*A61B 5/00* (2006.01)
*A61B 5/07* (2006.01)
*A61B 5/145* (2006.01)
*A61B 5/1459* (2006.01)
*A61B 5/1473* (2006.01)
*A61B 5/1455* (2006.01)

(52) U.S. Cl.
CPC ............ *A61B 5/002* (2013.01); *A61B 5/0031* (2013.01); *A61B 5/07* (2013.01); *A61B 5/1459* (2013.01); *A61B 5/1473* (2013.01); *A61B 5/14503* (2013.01); *A61B 5/14546* (2013.01); *A61B 5/14556* (2013.01); *A61B 5/14735* (2013.01)

(58) Field of Classification Search
CPC . A61B 5/14546; A61B 5/1455; A61B 5/1459; A61B 5/1468; A61B 5/1473; A61B 5/14735; A61B 5/14503
See application file for complete search history.

(56) References Cited

U.S. PATENT DOCUMENTS

| 3,996,345 A | 12/1976 | Ullman et al. |
| 4,603,209 A | 7/1986 | Tsien et al. |
| 4,714,763 A | 12/1987 | Theodoropulos |

(Continued)

FOREIGN PATENT DOCUMENTS

| EP | 1 065 250 A1 | 1/2001 |
| WO | 97/40104 A1 | 10/1997 |

(Continued)

OTHER PUBLICATIONS

"PCT International Search Report and Written Opinion", International Searching Authority, dated Jun. 6, 2016, pp. 1-11.

(Continued)

*Primary Examiner* — Christian Jang
(74) *Attorney, Agent, or Firm* — McDonnell Boehnen Hulbert & Berghoff LLP

(57) ABSTRACT

A system for measuring and/or monitoring an analyte present in interstitial fluid in skin is provided. The system includes a substrate that may be implanted into the skin and a reader device. The substrate includes a sensor comprising aptamer conjugates and is configured to obtain one or more measurements related to at least one analyte in interstitial fluid. The reader device is configured to detect the analyte in interstitial fluid via interaction with the substrate.

22 Claims, 14 Drawing Sheets

(56) References Cited

U.S. PATENT DOCUMENTS

| | | | |
|---|---|---|---|
| 4,774,339 | A | 9/1988 | Haugland et al. |
| 4,810,636 | A | 3/1989 | Corey |
| 4,812,409 | A | 3/1989 | Babb et al. |
| 4,849,362 | A | 7/1989 | DeMarinis et al. |
| 4,945,171 | A | 7/1990 | Haugland et al. |
| 4,981,977 | A | 1/1991 | Southwick et al. |
| 5,132,432 | A | 7/1992 | Haugland et al. |
| 5,187,288 | A | 2/1993 | Kang et al. |
| 5,227,487 | A | 7/1993 | Haugland et al. |
| 5,242,805 | A | 9/1993 | Naleway et al. |
| 5,248,782 | A | 9/1993 | Haugland et al. |
| 5,268,486 | A | 12/1993 | Waggoner et al. |
| 5,274,113 | A | 12/1993 | Kang et al. |
| 5,433,896 | A | 7/1995 | Kang et al. |
| 5,442,045 | A | 8/1995 | Haugland et al. |
| 5,451,343 | A | 9/1995 | Neckers et al. |
| 5,459,276 | A | 10/1995 | Kuhn et al. |
| 5,486,616 | A | 1/1996 | Waggoner et al. |
| 5,501,980 | A | 3/1996 | Katerinopoulos et al. |
| 5,569,587 | A | 10/1996 | Waggoner |
| 5,569,766 | A | 10/1996 | Waggoner et al. |
| 5,627,027 | A | 5/1997 | Waggoner |
| 5,696,157 | A | 12/1997 | Wang et al. |
| 5,798,276 | A | 8/1998 | Haugland et al. |
| 5,808,044 | A | 9/1998 | Brush et al. |
| 5,830,912 | A | 11/1998 | Gee et al. |
| 5,846,737 | A | 12/1998 | Kang |
| 5,877,310 | A | 3/1999 | Reddington et al. |
| 6,002,003 | A | 12/1999 | Shen et al. |
| 6,004,536 | A | 12/1999 | Leung et al. |
| 6,008,373 | A | 12/1999 | Waggoner et al. |
| 6,043,025 | A | 3/2000 | Minden et al. |
| 6,127,134 | A | 10/2000 | Minden et al. |
| 6,130,094 | A | 10/2000 | Waggoner et al. |
| 6,130,101 | A | 10/2000 | Mao et al. |
| 6,133,445 | A | 10/2000 | Waggoner et al. |
| 6,162,931 | A | 12/2000 | Gee et al. |
| 6,229,055 | B1 | 5/2001 | Klaubert et al. |
| 6,339,392 | B1 | 1/2002 | Ashihara |
| 6,562,632 | B1 | 5/2003 | Szalecki et al. |
| 6,664,047 | B1 | 12/2003 | Haugland et al. |
| 6,716,979 | B2 | 4/2004 | Diwu et al. |
| 6,974,873 | B2 | 12/2005 | Leung et al. |
| 6,977,305 | B2 | 12/2005 | Leung et al. |
| 2002/0193672 | A1* | 12/2002 | Walsh .............. A61B 5/14532 600/316 |
| 2004/0116977 | A1* | 6/2004 | Finch .............. A61N 1/36017 607/46 |
| 2005/0245799 | A1* | 11/2005 | Brauker ............ A61B 5/6882 600/347 |
| 2012/0088990 | A1* | 4/2012 | Bunge .............. A61B 5/14503 600/309 |
| 2013/0078733 | A1* | 3/2013 | Holmes .............. B01L 3/0217 436/174 |
| 2013/0338771 | A1* | 12/2013 | Boyden .............. A61F 2/12 623/8 |

FOREIGN PATENT DOCUMENTS

| | | |
|---|---|---|
| WO | 99/51702 A1 | 10/1999 |
| WO | 00/02048 A1 | 1/2000 |
| WO | 01/21624 A1 | 3/2001 |
| WO | 02/26891 A1 | 4/2002 |
| WO | 2014/123430 A1 | 8/2014 |
| WO | 2014/197729 A1 | 12/2014 |

OTHER PUBLICATIONS

Ghandehari, H., et al., "Biodegradable and pH Sensitive Hydrogels: Synthesis by a Polymer-Polymer Reaction", J. Macromol. Chem. Phys., Mar. 1996, vol. 197(3), pp. 965-980. (Abstract only).

Hwang, S., et al., "A Physically Transient Form of Silicon Electronics", Science, Sep. 28, 2012, vol. 337, pp. 1640-1644.

Ishihara, K., et al., "Glucose Induced Permeation Control of Insulin through a Complex Membrane Consisting of Immobilized Glucose Oxidase and a Poly(amine)", Polymer J., 1984, vol. 16(8), pp. 625-631.

Jeong, B., et al., "Biodegradable Block Copolymers as Injectable Drug-Delivery Systems", Nature, 1997, vol. 388, pp. 860-862. (Abstract only).

Lee, B., et al., "Virus-based Piezoelectric Energy Generation", Nature Nanotechnology, Jun. 2012, vol. 7, pp. 351-356, DOI:10.1038/NNANO.2012.69.

Meadows, D.L., "Design, Manufacture and Characterization of an Optical Fiber Glucose Affinity Sensor Based on an Homogeneous Fluorescence Energy Transfer Assay System", Analytica Chimica Acta, Jan. 16, 1993, vol. 280, pp. 21-30.

Nutiu, R., et al., "Engineering DNA Aptamers and DNA Enzymes with Fluorescence-Signaling Properties", Pure Appl. Chem., 2004, vol. 76(7-8), pp. 1547-1561.

Quinn, et al., "Biocompatible, Glucose-Permeable Hydrogel for In Situ Coating of Implantable Biosensors", Biomaterials, Dec. 1997, vol. 18(24), pp. 1665-1670. (Abstract only).

Quinn, C.P., et al., "Photo-Crosslinked Copolymers of 2-Hydroxyethyl Methacrylate, Poly(ethylene glycol) Tetra-Acrylate and Ethylene Dimethacrylate for Improving Biocompatibility of Biosensors", Biomaterials, Mar. 1995, vol. 16 (5), pp. 389-396. (Abstract only).

Richieri, Gary V., et al.,"A Flourescently Labeled Intestinal Fatty Acid Binding Protein", J. Biol. Chem., Nov. 25, 1992, vol. 267(33), pp. 23495-23501.

Sefah, Kwame, et al., "Development of DNA Aptamers Using Cell-SELEX", Nature Protocols, Jun. 1, 2010, vol. 5, pp. 1169-1185. (Abstract only).

Shen, Qinglin, et al., "Specific Capture and Release of Circulating Tumor Cells Using Aptamer-Modified Nanosubstrates", Advanced Materials, Mar. 12, 2013, vol. 25(16), pp. 2368-2373, DOI:10.1002/adma.201300082.

Tram, K., et al., "Lighting Up RNA-Cleaving DNAzymes for Biosensing", Journal of Nucleic Acids, Oct. 3, 2012,13 vol. 2012, Article ID 958683, 8 pages, doi:10.1155/2012/958683.

Vuyisich, M., et al., "Controlling Protein Activity with Ligand-Regulated RNA Aptamers", Chemistry & Biology, Aug. 2002, vol. 9, pp. 907-913.

"Biosensors: Fundamentals and Applications", Oxford Science Publications, Mar. 1, 1990, Edited by A.P.F. Turner, Isao Karube and George S. Wilson, published from Oxford University Press in 1988 (Aug. 6, 1987), 770 pages. (Abstract only).

* cited by examiner

APTAMER-BASED SENSORS, IMPLANTABLE DEVICES AND DETECTION SYSTEM

BACKGROUND

Unless otherwise indicated herein, the materials described in this section are not prior art to the claims in this application and are not admitted to be prior art by inclusion in this section.

A number of scientific methods have been developed to detect and/or measure one or more analytes in a person's blood. The presence or absence of a physiologically relevant analyte in the blood, or the presence at a particular concentration or range of concentrations, may be indicative of a medical condition or the person's state of health. Physiologically relevant analytes may include enzymes, hormones, proteins, cells or other molecules.

In a typical scenario, a person's blood is drawn and sent to a lab where a variety of tests are performed to measure various analyte levels and parameters in the blood. The variety of tests may be referred to as "blood work," where the blood is tested for the presence of various diseases, or analyte levels such as cholesterol levels, etc. For most people, the blood tests are infrequent, and an abnormal analyte level indicative of a medical condition may not be identified for some time after the blood work is performed.

Physiologically relevant analytes may also be present in a person's sweat and/or interstitial fluid. These analytes include sugars, salts, fatty acids, amino acids, coenzymes, hormones, neurotransmitters, and cell waste products.

SUMMARY

One aspect of the present disclosure provides a system. The system includes a substrate including a sensor, the sensor comprising aptamer conjugates, wherein the sensor is configured to obtain one or more measurements related to at least one analyte in interstitial fluid, and wherein the substrate is configured for implantation into skin; and a reader device, wherein the reader device is configured to detect the analyte in interstitial fluid via interaction with the substrate.

In some embodiments, the substrate may also include an antenna, which is capable of transmitting information related to the sensor-analyte interaction to the reader device. The information may include raw data which the reader device can manipulate to provide the presence/absence of an analyte or the concentration of an analyte.

In other embodiments, the substrate includes a component configured to undergo an optically-detectable change upon interaction with an analyte. The optically-detectable change may involve a change in at least one of optical absorption, reflectivity, or fluorescence. The substrate can be used in conjunction with a reader device configured to detect the optically-detectable change. The reader device may include a light source configured to direct light toward the substrate, and a photodetector configured to detect light from the substrate. The detected optical change can be used to determine the presence/absence of an analyte or the concentration of an analyte.

In another aspect, the present disclosure provides a method for receiving, by a substrate, a signal from a reader device, wherein the substrate comprises a sensor, the sensor comprising aptamer conjugates, and wherein the substrate is implanted into skin; performing, by the sensor, in response to the signal, a measurement related to at least one analyte in interstitial fluid; and communicating, by the substrate, data indicative of the measurement to the reader device.

In yet another aspect, the present disclosure provides a method for transmitting, by a reader device, a signal to a substrate implanted into skin, the substrate comprising a sensor, the sensor comprising aptamer conjugates, wherein the sensor is configured to obtain one or more measurements related to at least one analyte in interstitial fluid; and receiving, by the reader device, a responsive signal from the substrate, wherein the responsive signal indicates the one or more measurements related to the analyte interstitial fluid.

These as well as other aspects, advantages, and alternatives, will become apparent to those of ordinary skill in the art by reading the following detailed description, with reference where appropriate to the accompanying drawings.

DETAILED DESCRIPTION

I. Overview

Figure 1:
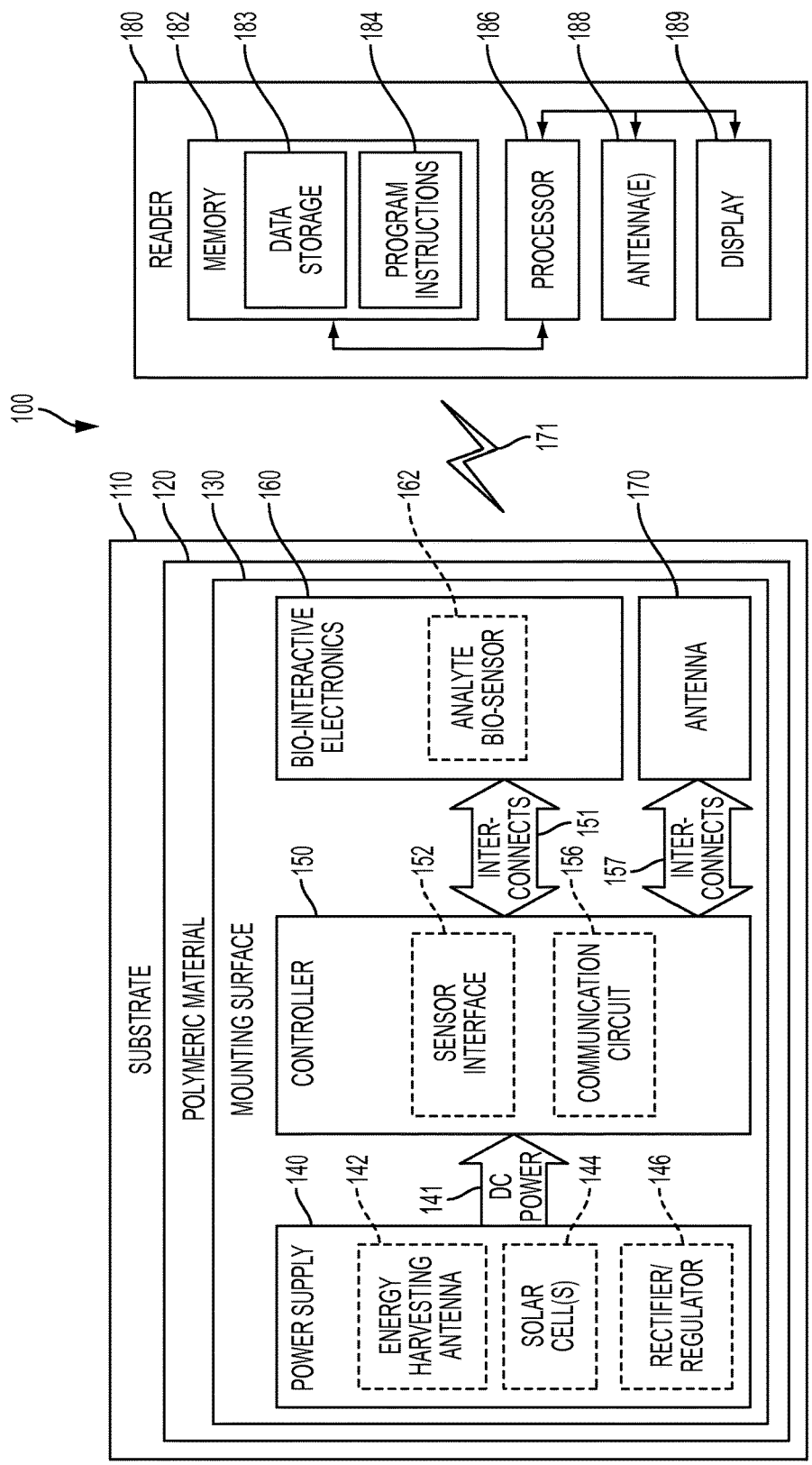
FIG. 1 is a block diagram of an example system that includes a substrate in wireless communication with a reader device, in accordance with an example embodiment.

A system for monitoring analyte levels can include a substrate and a reader device. The substrate may include a sensor, control electronics and an antenna embedded in a polymeric material, and can be configured to interact with an analyte. The polymeric material may enable the substrate to be an implantable medical device. The control electronics can operate the sensor to perform readings and can operate the antenna to wirelessly communicate the readings from the sensor to a reader device via the antenna.

A substrate that is "implantable" refers to a substrate that is in contact with the inner skin layer, i.e., the epidermis, inter-dermis, or dermis. When the substrate is in contact with an inner skin layer such as the dermis, the substrate may have direct contact with interstitial fluid. For example, the substrate may be implantable or injectable.

In some examples, the polymeric material can be in the form of a layer, such as a patch. The substrate components can be embedded near the periphery of the polymeric material to provide optimal interaction with an analyte of interest. The sensor can be arranged on the substrate to face inward, toward the skin surface, so as to generate clinically relevant readings from the interstitial fluid interposed between the polymeric material and the skin layer such as the dermis. In some examples, the sensor is entirely embedded within the polymeric material. For example, an optical sensor that includes aptamer conjugates can be embedded in the polymeric material and situated such that the sensor electrodes are less than 10 micrometers from the polymeric surface configured to be implanted into the skin. The sensor can generate a response signal indicative of a concentration of an analyte that diffuses through the polymeric material to the sensor electrodes.

Interstitial fluid contains a variety of inorganic electrolytes (e.g., $Ca^{2+}$, $Mg^{2+}$, $Cl^-$), organic components (e.g., glucose, lactate, proteins, lipids, etc.), and so on that can be used to diagnose health states. A system including the above-mentioned sensor can be configured to measure one or more of these analytes can thus provide a convenient non-invasive platform useful in diagnosing and/or monitoring health states. For example, a system can be configured to sense glucose and can be used by diabetic individuals to measure/monitor their glucose levels. In some embodiments, the sensor can be configured to measure additional or other conditions other than analyte levels, e.g., heart rate or body temperature.

An external reader device or "reader" can radiate electromagnetic radiation to power the sensing platform (i.e., sensor) of the substrate. The reader may thereby control the operation of the system by controlling the supply of power to the sensor. In some examples, the reader can operate to intermittently interrogate the sensor to provide a reading by radiating sufficient radiation to power the sensor to obtain a measurement and communicate the result. The reader can also store the sensor results communicated by the sensor. In this way, the reader can acquire a series of analyte concentration measurements over time without continuously powering the sensor.

In some embodiments, the electromagnetic radiation is radio frequency (RF), which may provide power to the sensor. In some embodiments, the reader may optically communicate with the substrate, and the radiation may be light. For example, upon interaction with an analyte, the substrate may undergo a change in an optical property that can be detected by the reader. Example optical properties include optical absorption, reflectivity and fluorescence. In some examples, the wavelength of light (e.g., visible, IR, UV, etc.) provided by the reader may depend on the optical property of the substrate.

The analyte concentration information can be sent from the reader to a display device. The display device could be, for example, a wearable, laptop, desktop, handheld, or tablet computer, a mobile phone, or a subsystem of such a device. In some embodiments, the reader is also the display device. The display device can include a processing system; e.g., a central processing unit (CPU), and a non-transitory computer readable medium configured to store at least program instructions. One example of a wearable computer is a head-mountable display (HMD). The HMD can be a device that is capable of being worn on the head and places a display in front of one or both eyes of the wearer. The display device can store the data received from the reader, perhaps process the data, and generate display(s) based on the received and/or processed data.

In some embodiments, the reader and the display device can be configured with configuration data to perform analyte-related processing. For example, the reader can include configuration data such as current measurement data for various levels of glucose concentration. Based on this configuration data, the reader can determine a glucose concentration for the wearer. Also, the wearer can provide blood glucose concentration(s) and corresponding interstitial fluid glucose concentration(s) for the wearer to the display device (for example, during configuration), and the display device can determine relationships between blood glucose concentration(s) and interstitial fluid glucose concentration(s).

During operation of these embodiments, the substrate can generate and send current analyte data to the reader. The reader can then process the current data to generate analyte concentration(s) data and send the concentration(s) data to the display device. Then, the display device can be configured to receive concentration(s) data from the reader and generate corresponding blood-analyte concentration(s). In particular embodiments, either the reader or the display device can take current analyte data as inputs and generate blood-analyte concentration(s) as output(s); i.e., all processing can take place at either the reader or display device.

In some embodiments, the reader is a wearable device, such as an arm or wrist band, and can be worn directly over the area above the implanted substrate and provide power and/or receive measurements continuously or semi-continuously.

Configuring the reader to be frequently worn in proximity to one or more substrate enables the system to have a reliable external power source and/or storage for analyte data collection, processing of analyte data, and transmission of unprocessed and/or processed analyte data to additional devices; e.g., the above-mentioned display device. Thus, the herein-described reader can provide valuable support functionality, including but not limited to power, communication, and processing resources, to enhance use of a substrate with embedded sensors, while enabling consequent reduction of support functions in the substrate. This reduction of support functions on the substrate may free resources on the substrate and enable addition of more and/or different sensors and to provide for other functionality on the substrate.

II. Example System

FIG. 1 is a block diagram of a system 100 that includes a substrate 110 in wireless communication with a reader 180. The exposed regions of the substrate 110 are made of a polymeric material 120 formed to be incorporated beneath the skin surface. A mounting surface 130 is embedded in the polymeric material 120 to provide a mounting surface for a power supply 140, a controller 150, bio-interactive electronics 160, and a communication antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the substrate 110. The antenna 170, the controller 150, the power supply 140, and the bio-interactive electronics 160 can all be situated on the embedded mounting surface 130. The substrate 110 includes electronics and is configured to be implanted into skin, it is also referred to herein as an implanted electronics platform.

The polymeric material 120 can be a substantially transparent material to allow for optical communication between the substrate and the reader and can include one or more biocompatible materials, such as those employed for use in implantable devices involving direct contact within the skin. The polymeric material 120 can optionally be formed in part from such biocompatible materials or can include an outer coating with such biocompatible materials. In some embodiments, the external surface of the polymeric material 120 may be water proof to allow for prolonged use of the system in skin. However, in other embodiments, the polymeric material 120 can be configured to deteriorate over a desired period of time.

The mounting surface 130 includes one or more surfaces suitable for mounting the bio-interactive electronics 160, the controller 150, the power supply 140, and the antenna 170. The mounting surface 130 can be employed both as a mounting platform for chip-based circuitry (e.g., by flip-chip mounting to connection pads) and/or as a platform for patterning conductive materials (e.g., gold, platinum, palladium, titanium, copper, aluminum, silver, metals, other conductive materials, combinations of these, etc.) to create electrodes, interconnects, connection pads, antennae, etc. In some embodiments, substantially transparent conductive materials (e.g., indium tin oxide) can be patterned on the mounting surface 130 to form circuitry, electrodes, etc. For example, the antenna 170 can be formed by forming a pattern of gold or another conductive material on the mounting surface 130 by deposition, photolithography, electroplating, etc. Similarly, interconnects 151, 157 between the controller 150 and the bio-interactive electronics 160, and between the controller 150 and the antenna 170, respectively, can be formed by depositing suitable patterns of conductive materials on the mounting surface 130. A combination of microfabrication techniques including, without limitation, the use of photoresists, masks, deposition techniques, and/or plating techniques can be employed to pattern materials on the mounting surface 130. The mounting surface 130 can be a relatively rigid material, such as polyethylene terephthalate ("PET") or another material configured to structurally support the circuitry and/or chip-based electronics within the polymeric material 120. The substrate 110 can alternatively be arranged with a group of unconnected substrates rather than a single substrate. For example, the controller 150 and a bio-sensor or other bio-interactive electronic component can be mounted to one substrate, while the antenna 170 is mounted to another substrate and the two can be electrically connected via the interconnects 157.

The substrate 110 can be shaped in various ways, including being substantial flat, circular, square or rectangular. In some embodiments, the substrate 110 can be shaped to conform to the characteristics of a desired mounting location. The dimensions of the substrate 110 can be sufficient to provide a mounting platform for the embedded electronics components. The mounting surface 130 can have a thickness sufficiently small to allow the mounting surface 130 to be embedded in the polymeric material 120 without influencing the profile of the substrate 110. The mounting surface 130 can have a thickness sufficiently large to provide structural stability suitable for supporting the electronics mounted thereon. For example, the mounting surface 130 can be shaped to accommodate the dimensions of the substrate 110, with a thickness of about 50 micrometers. The mounting surface 130 can optionally be aligned with any curvature of the substrate 110. The power supply 140 is configured to harvest ambient energy to power the controller 150 and bio-interactive electronics 160. For example, a radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. The energy harvesting antenna 142 can optionally be a dual-purpose antenna that is also used to communicate information to the reader 180. That is, the functions of the communication antenna 170 and the energy harvesting antenna 142 can be accomplished with the same physical antenna.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected in parallel across the outputs of the rectifier 146 to regulate the DC supply voltage 141 and configured to function as a low-pass filter.

The controller 150 is turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the substrate 110. The interaction could involve the use of one or more components, such an analyte bio-sensor 162, in bio-interactive electronics 160 to obtain input from the biological environment.

In one example, the controller 150 includes a sensor interface module 152 that is configured to operate analyte bio-sensor 162. In one example, the analyte bio-sensor 162 is an amperometric electrochemical sensor that includes a working electrode and a reference electrode. A voltage can be applied between the working and reference electrodes to cause an analyte to undergo an electrochemical reaction (e.g., a reduction and/or oxidation reaction) at the working electrode. The electrochemical reaction can generate an amperometric current that can be measured through the working electrode. The amperometric current can be dependent on the analyte concentration. Thus, the amount of the amperometric current that is measured through the working electrode can provide an indication of analyte concentration. In some embodiments, the sensor interface module 152 can be a potentiostat configured to apply a voltage difference between working and reference electrodes while measuring a current through the working electrode.

In some instances, a reagent can also be included to sensitize the electrochemical sensor to one or more desired analytes. For example, a layer of a catalytic aptamer, e.g., DNAzyme, or glucose oxidase ("GOx") proximal to the working electrode can catalyze glucose oxidation to generate hydrogen peroxide ($H_2O_2$). The hydrogen peroxide can then be electro-oxidized at the working electrode, which releases electrons to the working electrode, resulting in an amperometric current that can be measured through the working electrode.

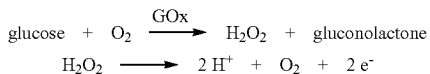

$$H_2O_2 \longrightarrow 2\,H^+ + O_2 + 2\,e^-$$

The current generated by either reduction or oxidation reactions is approximately proportionate to the reaction rate. Further, the reaction rate is dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate is approximately proportionate to the concentration of the analyte molecules. The current measured through the working electrode thus provides an indication of the analyte concentration.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the substrate 110 is configured to indicate an output from a bio-sensor by modulating an impedance of the antenna 170 in a manner that is perceivable by the reader 180. For example, the communication circuit 156 can cause variations in the amplitude, phase, and/or frequency of backscatter radiation from the antenna 170, and such variations can be detected by the reader 180.

The controller 150 is connected to the bio-interactive electronics 160 via interconnects 151. For example, where the controller 150 includes logic elements implemented in an integrated circuit to form the sensor interface module 152, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the substrate 110 can be arranged with one or more of the functional modules ("sub-systems") implemented in a single chip, integrated circuit, and/or physical component. For example, while the rectifier/regulator 146 is illustrated in the power supply block 140, the rectifier/regulator 146 can be implemented in a chip that also includes the logic elements of the controller 150 and/or other features of the embedded electronics in the substrate 110. Thus, the DC supply voltage 141 that is provided to the controller 150 from the power supply 140 can be a supply voltage that is provided to components on a chip by rectifier and/or regulator components located on the same chip. That is, the functional blocks in FIG. 1 shown as the power supply block 140 and controller block 150 need not be implemented as physically separated modules. Moreover, one or more of the functional modules described in FIG. 1 can be implemented by separately packaged chips electrically connected to one another.

Additionally or alternatively, the energy harvesting antenna 142 and the communication antenna 170 can be implemented with the same physical antenna. For example, a loop antenna can both harvest incident radiation for power generation and communicate information via backscatter radiation.

The reader 180 can include one or more antennae 188 to send and receive wireless signals 171 to and from the substrate 110. In some embodiments, reader 180 can communicate using hardware and/or software operating according to one or more standards, such as, but not limited to, a RFID standard, a Bluetooth standard, a Wi-Fi standard, a Zigbee standard, etc.

Reader 180 can also include a computing system with a processor 186 in communication with a memory 182. Memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the analyte bio-sensor 162), program settings (e.g., to adjust behavior of the substrate 110 and/or reader 180), etc. The memory 182 can also include program instructions 184 for execution by the processor 186 to cause the reader 180 to perform processes specified by the instructions 184. For example, the program instructions 184 can cause reader 180 to provide a user interface that allows for retrieving information communicated from the substrate 110 (e.g., sensor outputs from the analyte bio-sensor 162). The reader 180 can also include one or more hardware components for operating the antenna 188 to send and receive the wireless signals 171 to and from the substrate 110. For example, oscillators, frequency injectors, encoders, decoders, amplifiers, filters, etc. can drive the antenna 188 according to instructions from the processor 186.

The reader can also include a display 184 capable of providing a visual representation of the interaction of the substrate with an analyte. For example, the display 184 can present textual or graphical information. In some embodiments, the display 184 can provide a visual indication the measured physiological parameter(s), such as, the concentration of a measured analyte. The display may also be configured to provide an alert or recommendation when an analyte concentration does not fall within a predetermined range of concentration values.

In some embodiments, reader 180 can be a smart phone, digital assistant, or other portable computing device with wireless connectivity sufficient to provide the wireless communication link 171. In some embodiments, the reader can be a wearable device configured to measure a biological analyte. In other embodiments, reader 180 can be implemented as an antenna module that can be plugged in to a portable computing device; e.g., in scenarios where the communication link 171 operates at carrier frequencies not commonly employed in portable computing devices. In other embodiments, the reader 180 can be a special-purpose device configured to be worn relatively near to the substrate to allow the wireless communication link 171 to operate with a low power budget. For example, the reader 180 can be integrated in a piece of clothing or jewelry such as a shoe, sweatband, watch, bracelet or cuff.

In one embodiment, the system 100 can be operated to monitor the analyte concentration in interstitial fluid. Interstitial fluid includes components that are continuously exchanged between plasma and interstitial fluids across the walls of capillaries. The components may include biomarkers found in blood that can be analyzed to characterize a person's health condition(s). The components may include ions such as magnesium, calcium, sodium and potassium, solutes, sugars such as glucose, lactate, urea, salts, fatty acids, amino acids, coenzymes, hormones, neurotransmitters, as well as waste products from the cells. The biomarker concentrations in interstitial fluid can be systematically different than the corresponding concentrations of the biomarkers in the blood, but a relationship between the two concentration levels can be established to map interstitial fluid biomarker concentration values to blood concentration levels.

Thus, measuring interstitial fluid analyte concentration levels provides a non-invasive technique for monitoring biomarker levels in comparison to blood sampling techniques performed by lancing a volume of blood to be analyzed outside a person's body. Moreover, the system disclosed here can be operated substantially continuously to enable real time monitoring of analyte concentrations.

In one embodiment, to perform a reading with the system 100 configured as an implanted analyte monitor, the reader 180 can emit radio frequency radiation 171 that is harvested to power the substrate 110 via the power supply 140. Radio frequency electrical signals captured by the energy harvesting antenna 142 (and/or the communication antenna 170) are rectified and/or regulated in the rectifier/regulator 146 and a regulated DC supply voltage 147 is provided to the controller 150. The radio frequency radiation 171 thus turns on the electronic components within the substrate 110. Once turned on, the controller 150 operates the analyte bio-sensor 162 to measure an analyte concentration level. For example, the sensor interface module 152 can apply a voltage between a working electrode and a reference electrode in the analyte bio-sensor 162. The applied voltage can be sufficient to cause the analyte to undergo an electrochemical reaction at the working electrode and thereby generate an amperometric current that can be measured through the working electrode. The measured amperometric current can provide the sensor reading ("result") indicative of the analyte concentration. The controller 150 can operate the antenna 170 to communicate the sensor reading back to the reader 180 (e.g., via the communication circuit 156). The sensor reading can be communicated by, for example, modulating an impedance of the communication antenna 170 such that the modulation in impedance is detected by the reader 180. The modulation in antenna impedance can be detected by, for example, backscatter radiation from the antenna 170.

In some embodiments, the system 100 can operate to non-continuously ("intermittently") supply energy to the substrate 110 to power the controller 150 and electronics 160. For example, radio frequency radiation 171 can be supplied to power the substrate 110 long enough to carry out an analyte concentration measurement and communicate the results. For example, the supplied radio frequency radiation can provide sufficient power to apply a potential between a working electrode and a reference electrode sufficient to induce electrochemical reactions at the working electrode, measure the resulting amperometric current, and modulate the antenna impedance to adjust the backscatter radiation in a manner indicative of the measured amperometric current. In such an example, the supplied radio frequency radiation 171 can be considered an interrogation signal from the reader 180 to the substrate 110 to request a measurement. By periodically interrogating the substrate 110 (e.g., by supplying radio frequency radiation 171 to temporarily turn the device on) and storing the sensor results (e.g., via the data storage 183), the reader 180 can accumulate a set of analyte concentration measurements over time without continuously powering the substrate 110.

III. Example Electrochemical Sensor

Figure 2A:
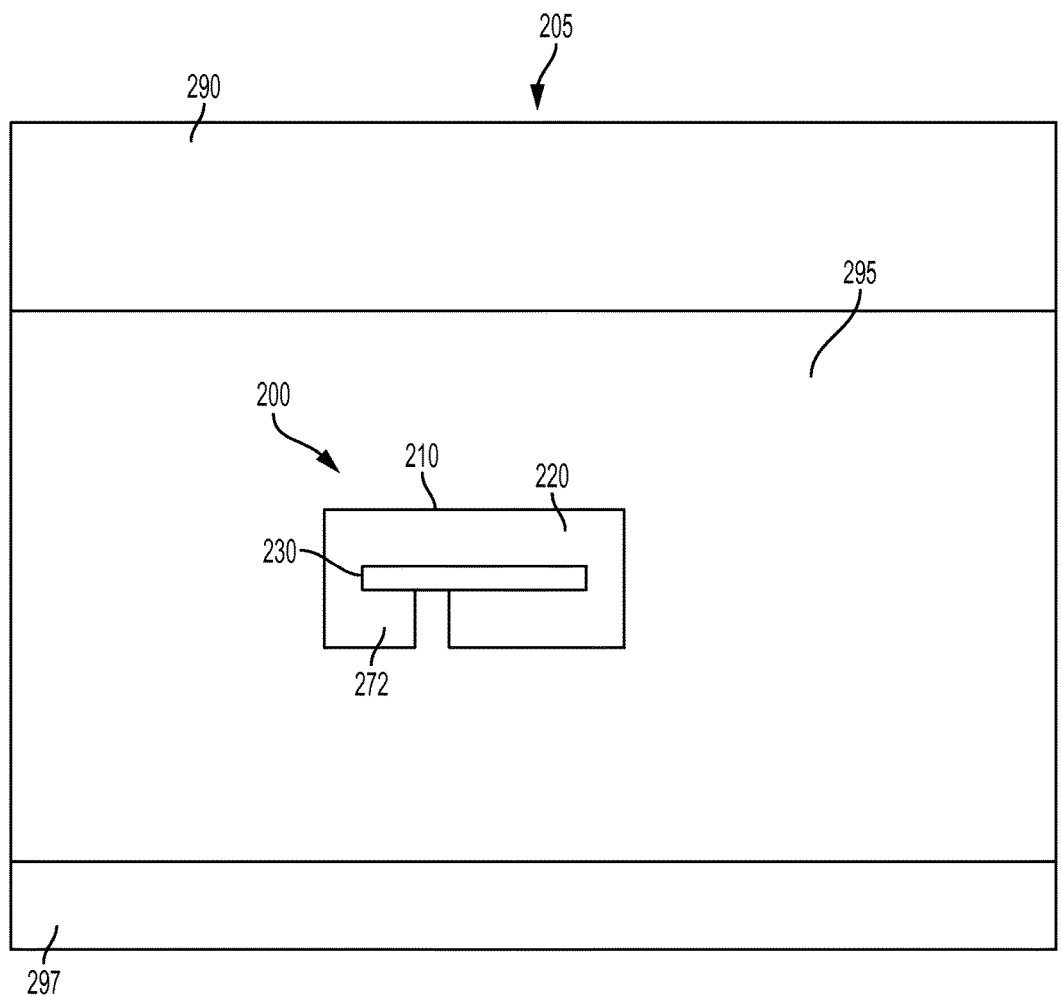
FIG. 2A is a side cross-section view of an example substrate implanted into the dermal layer of the skin of an arm.
Figure 2B:
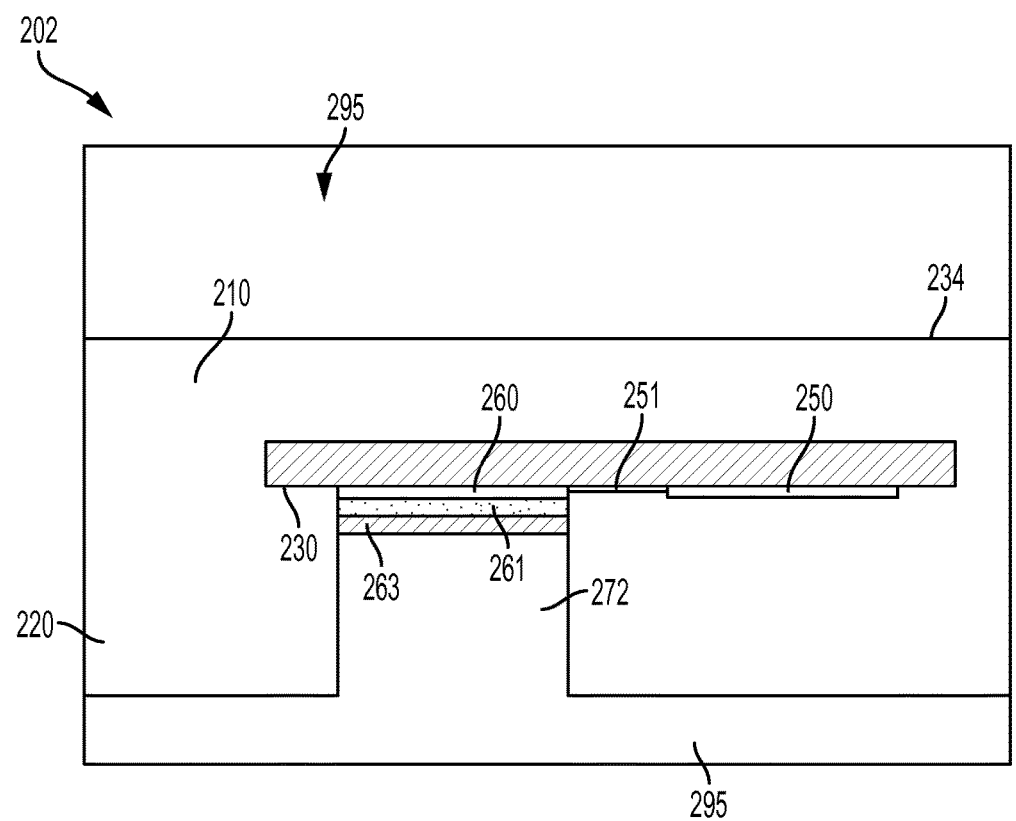
FIG. 2B is a side cross-section view enhanced to show the components of the example substrate when implanted as shown in FIG. 2A.

As shown in the cross-sectional views 200 and 202 in FIGS. 2A and 2B, the substrate 210 can be implanted into the dermal region 295 of skin 205 which also includes the epidermis 290 and subcutaneous fat layer 297. It is noted that relative dimensions in FIG. 2A are not necessarily to scale, but have been rendered for purposes of explanation only in describing the arrangement of the example implantable substrate 210. The substrate 210 can have an internal mounting surface 230, to which electronic components and/or patterned conductive materials are mounted, all of which may be embedded in a polymeric material 220. As shown in FIG. 2B, the bio-interactive electronics 260, controller 250, and a conductive interconnect 251 are mounted on the internal mounting surface 230 such that the bio-interactive electronics 260 are accessible through a channel 272. With this arrangement, the bio-interactive electronics 260 can receive interstitial fluid through the channel 272.

Bio-interactive electronics 260 can be selectively sensitive to an analyte by localizing an ionophore, metal oxide film, or reagent such as a catalytic aptamer that selectively interacts with the analyte near the bio-interactive electronics 260. As shown in FIG. 2B, a sensitizing layer 261 can be located proximate to the bio-interactive electronics 260. The sensitizing layer 261 can include elements other than elements that selectively interact with the analyte; for example, the sensitizing layer 261 could include a polymer that is permeable to the analyte. An analyte-selective element of the sensitizing layer 261 could be absorbed in, adsorbed onto, covalently bonded to, or otherwise disposed on or within such a polymer. The sensitizing layer 261 can include aptamers conjugated to labels such as nanoparticles of analyte-selective elements adsorbed onto, covalently bonded to, sintered to, chemically or physically deposited onto, electroplated onto, or otherwise disposed on an electrode of the bio-active electronics 260.

In some examples, the sensitizing layer 261 can include one or more ionophores that selectively interact with an ion. The ionophores could be covalently bound onto backbones of a crosslinked, ion-permeable polymer formed onto an electrode of the bio-interactive electronics 260. In some examples, the ion is potassium, and the ionophore includes one or more of valinomycin, bis[(benzo-15-crown-4)-4'-ylmethyl]pimelate), 2-dodecyl-2-methyl-1,3-propanediyl-bis-[N-(5'-nitro(benzo-15-crown-5)-4'-yl)carbamate], and 4-tert-butyl-2,2,14,14-tetrahomo-4a,14a-dioxacalix[4]arene-tetraacetic acid tetra-tert-butyl ester. Potassium from interstitial fluid 270 can diffuse through the channel 272 and reversibly bind to the ionophore until an electrochemical equilibrium is reached based on the concentration of potassium in the interstitial fluid, resulting in an equilibrium potentiometric voltage that can be measured between the working electrode and the reference electrode.

In some examples, the sensitizing layer 261 can include a thin film including a metal or a metal oxide that selectively interacts with the analyte. The thin film can localized on and put into electrical contact with a working electrode of the bio-interactive electronics 260 by being electroplated, chemical-vapor deposited, physical-vapor deposited, sintered, welded, soldered, or some other method of securing the thin film to and ensuring an electrical connection with the electrode. Forming the thin film could include more than one process; for example, the thin film could be a metal oxide, and the thin film could be formed by depositing a metal on the electrode and then exposing the metal to an oxidizing agent such that a surface of the deposited metal become the metal oxide. In some examples, the analyte is phosphate, and the sensitizing layer 261 includes cobalt oxide. The cobalt oxide can engage in a redox reaction with phosphate and water from the interstitial fluid that diffuses through the channel 272, forming cobalt phosphate and hydroxide ions. This reaction can proceed until an electrochemical equilibrium is reached based on the concentration of phosphate in the interstitial fluid, resulting in an equilibrium potentiometric voltage that can be measured between the working electrode and the reference electrode.

A protective layer 263 which is permeable to the analyte can be disposed on the sensitizing layer 261. The protective layer 263 can be composed of a polymer that is permeable to the analyte. The polymer may be formulated to include porogens to tailor the permeability to the analyte of the protective layer 263 for a specific application. In some examples, the sensitizing layer 261 could be selectively sensitive to one or more analytes in addition to the analyte of interest. In those examples, the protective layer 263 could be configured to be impermeable to the one or more analytes, such that only the analyte of interest was able to both diffuse through the protective layer 263 and interact with the sensitizing layer 261.

In some embodiments, the polymer material 220 includes the properties of the sensitizing layer 261 and protecting layer 263. Where polymer material 220 includes the properties of the sensitizing layer 261 and protective layer 263, the presence of a separate sensitizing layer 261 and protective layer 263 can be eliminated. In such embodiments, where the analyte is capable of diffusing the polymer material 220 to interact with the bio-interactive electronics 260, the channel 272 may not be present.

Figure 2C:
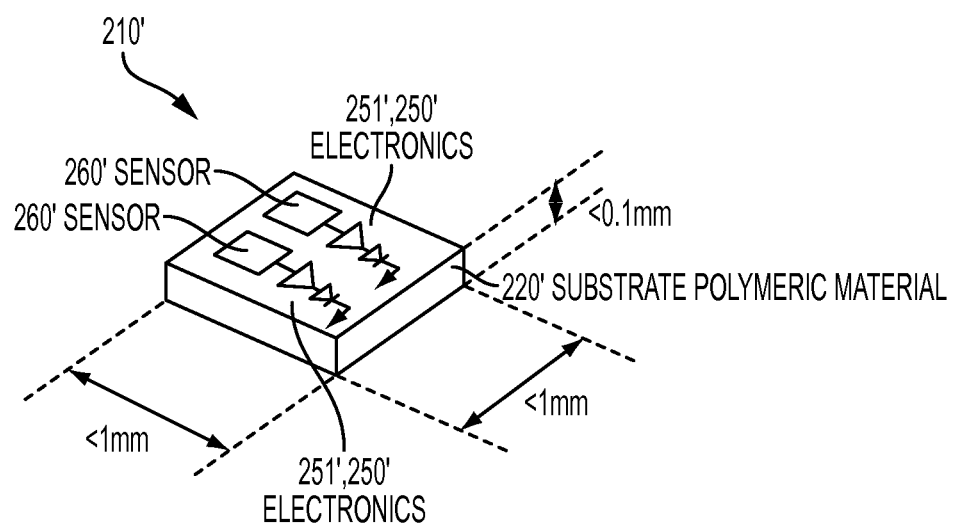
FIG. 2C is a top view of an example substrate.

FIG. 2C illustrates a top view 204' of an alternative example substrate 210' which includes polymer material 220' with embedded surface bio-interactive electronics 260', conductive interconnect 251' and controller 250' that are exposed on one surface. In some embodiments, a sensitizing layer 261' and protective layer 263' can be present over electronics 260'. In other embodiments, a protective layer 263' can be present over the electronics 260', conductive interconnect 251' and controller 250'.

The dimensions of the substrate including the sensor can vary as desired. In one embodiment, the dimensions of the substrate are such that the substrate can be directly injected into the skin using a suitable injection device such as a syringe having a narrow bore hypodermic needle. Generally, the dimensions of the substrate can range less than 1 mm lengthwise, less than 1 mm widthwise, and less than 0.1 mm thickness, usually less than 1 mm from its largest dimension, usually around less than 1 mm in its largest dimension.

In another embodiment, the bio-interactive electronics 260 include components that allow for the optical detection of an analyte by the reader. For example, the bio-interactive electronics 260 may include assay components that undergo a detectable change, e.g., in optical absorption, reflectivity or fluorescence, upon interaction with an analyte. In such embodiments, the reader may be placed over the substrate and measure the analyte by detecting the change in optical property. The reader device may include a light source configured to direct light toward the substrate, and a photodetector configured to detect light from the substrate.

The substrate may remain in place when implanted into the skin and removed whenever desired. Alternatively, the substrate can be made of a biodegradable material or polymer and thus remain transiently at the implant site. The substrate may include components of an assay having a readout which is an optical signal detectable or measurable transdermally by external optical means. In another alternative, the substrate can be embedded within a matrix of biodegradable material or polymer, retained by an envelope of biodegradable material or polymer, or covered or coated with a biodegradable material or polymer.

The assay components can include an aptamer conjugated to a label, polymer and/or substrate or a component of the substrate (also referred to as aptamer conjugate) that has a specific affinity to bind to or interact with a specific analyte. The term "binding" is understood in its broadest sense to include any detectable interaction between an analyte and an aptamer conjugate. The aptamer can be conjugated to the polymer covalently or otherwise attaching or associating the aptamer with the polymer. That is, the aptamer may be entrapped or immobilized physically or chemically within the polymer in any manner that allows analyte-induced conformational change of the aptamers, retention of the aptamers in or on the polymers to prevent loss of the aptamer, and to provide a stable, continuous and reversible sensor response to changing concentrations of the target analyte of interest. Suitable polymers such as hydrogels are permeable to the analyte, prevent interference from other biomolecules, are biocompatible and biostable. Other molecules such as fluorophores or autofluorescent or luminescent markers or other optical agents or non-optical contrast agents (e.g., acoustic impedance contrast, RF contrast and the like), which may assist in interrogating the aptamer conjugates in vivo may be attached to the aptamer. For instance, the aptamer conjugates may include a chemiluminescent marker configured to produce a response signal in the form of luminescence radiation produced in response to a chemical reaction initiated, at least in part, by the binding of the target analyte to the aptamer.

In some embodiments, the bio-interactive electronics 260, controller 250, and a conductive interconnect 251 and all other electronic components including a power source are transient and can be manufactured from materials such as magnesium for conductors, magnesium oxide, silicon dioxide and mono-crystalline silicon that degrade in the presence of water and disappear in the body via reabsorption. Silk, which is water soluble and enzymatically degradable, can be used for the substrate. See, for instance, Hwang et al., Science, 2012, Vo. 337, pp. 1640-1644, incorporated by reference in its entirety, describing transient electronic components based on transient silicon-based metal oxide semiconductor (CMOS) technology.

The system may further include one or more data collection systems for interrogating, in a non-invasive manner, the aptamer conjugates present in the sensor. In one example, the system includes a detector configured to detect a response signal transmitted from the sensor. The response signal can include both an analyte response signal, which can be related to the interaction of the one or more target analytes with the aptamer conjugates, and a background noise signal. For example, the aptamer conjugates may include a chemiluminescent marker configured to produce a response signal in the form of luminescence radiation produced in response to a chemical reaction initiated, at least in part, to the binding of the target analyte to the aptamer conjugate.

In some examples, the system may also include an interrogating signal source for transmitting an interrogating signal that can penetrate into the sensor following exposure to the analyte and a detector for detecting a response signal that is transmitted from the sensor, in response to the interrogating signal. The interrogating signal can be any kind of signal that is benign to the patient, such as electromagnetic, magnetic, optic, acoustic, thermal, mechanical, electric and results in a response signal that can be used to measure a physiological parameter or, more particularly, that can detect the binding or interaction of the clinically-relevant analyte to the aptamer conjugates. In one example, the interrogating signal is a radio frequency (RF) signal and the response signal is a magnetic resonance signal, such as nuclear magnetic resonance (NMR). In another example, where the aptamer conjugates include a fluorophore, the interrogating signal is an optical signal with a wavelength that can excite the fluorophore in the sensor (e.g., a wavelength in the range of about 500 to about 1000 nanometers), and the response signal is fluorescence radiation from the fluorophore that can reach the detector. In another example, where the aptamer conjugates are labeled with particles of an electrically conductive material or a magnetically lossy material, the interrogation signal may be a time-varying magnetic field or a radio frequency (RF) electromagnetic signal, with sufficient signal power to rapidly heat the particles. The response signal may be an acoustic emission from the particles, caused by rapid thermal expansion of the particles, or caused by cavitation of the liquid medium in contact with the particles. As described above, in some cases, an interrogating signal may not be necessary to produce an analyte response signal.

In some cases, an interrogating signal is not necessary to measure one or more of the physiological parameters and, therefore, the wearable device 100 may not include a signal source 170. For example, the aptamer conjugates can include an autofluorescent or luminescent marker, such as a fluorophore, that will automatically emit a response signal indicative of the binding of the clinically-relevant analyte to the aptamer conjugates, without the need for an interrogating signal or other external stimulus. In some examples, the aptamer conjugates may include a chemiluminescent marker configured to produce a response signal in the form of luminescence radiation produced in response to a chemical reaction initiated, at least in part, to the binding of the target analyte to the aptamer.

Additionally, the system may further include a modulation source configured to modulate the analyte response signal. The modulation source can be configured to modulate the analyte response signal differently than the background noise signal. To this end, the modulation may help to discern between the target analyte and, essentially, everything else in the body by, for example, increasing the signal-to-noise ratio. Generally, the modulation may include any spatial, temporal, spectral, thermal, magnetic, mechanical, electrical, acoustic, chemical, or electrochemical, etc. modulation technique or any combination thereof.

In some scenarios, it may also be useful to detect and distinguish both the analyte response signal—related to aptamer conjugates bound to or interacting with target analyte(s)—and an "unbound" aptamer conjugate signal—related to aptamer conjugates not bound to or interacting with target analyte(s). For example, in some measurement or characterization schemes, it may be useful to determine the percentage of aptamer conjugates present in the sensor that have bound to the target analyte. In such cases, the modulation source may be configured to modulate the analyte response signal differently than the unbound aptamer conjugate signal.

The elements of the system, namely the type of modulation, the types of aptamers and target analytes may all be interrelated. Ultimately, the type of aptamer used to detect a particular target analyte may depend, to some extent, on the characteristics of the target analyte (i.e., type, size, shape, affinities, etc.), the chosen type of modulation (i.e., spatial, spectral, thermal, magnetic, mechanical, chemical, etc.), and/or the mode of interrogation (optical, acoustic, magnetic, RF, etc.).

IV. Illustrative Aptamer Conjugates

In some examples, the wearable devices described herein obtain at least some of the health-related information by detecting the binding of a clinically-relevant analyte to the aptamer conjugates. The conjugates can include polymers such as hydrogels which entrap or immobilize the aptamers physically or chemically to prevent loss of the aptamer, and to provide a stable, continuous and reversible sensor response to changing concentrations of the target analyte of interest. The conjugates can be prepared by covalently attaching or non-covalently immobilizing one or more aptamers designed to selectively bind or otherwise recognize a particular clinically-relevant analyte with a polymer. The aptamers may be labeled with fluorophores, autofluorescent or luminescent markers or other agents including optical agents or non-optical contrast agents which can be used to detect a response signal related to the interaction of one or more target analytes with the aptamer conjugates, with or without an interrogation signal. The binding or release of the aptamer conjugate and target analyte can trigger a conformational change to cause a more stable conformation that permits subsequent binding of a detectable agent such as a fluorophore, increase or decrease fluorescence via FRET, or release/binding of a secondary detectable molecule. Furthermore, the polymer may be functionalized with one or more aptamers to increase avidity to a target analyte or to detect multiple different targets. By entrapping or immobilizing the aptamers into a polymer matrix or scaffold, a biosensor can be localized to a specific location in the body to minimize or eliminate biofouling and/or immune responses.

i. Aptamers

Sometimes referred to as "synthetic antibodies," aptamers are pre-selected single-stranded oligonucleotide (e.g., DNA or RNA) or peptide molecules that bind to specific target molecules including proteins and peptides with affinities and specificities that are comparable to antibodies. These molecules can assume a variety of shapes due to their propensity to form helices and single-stranded loops with specific binding pockets, explaining their versatility in binding to diverse targets. Their specificity and characteristics are not directly determined by their primary sequence but by their tertiary structure which is analogous to the globular shape of tRNA. Aptamers have a wide range of applications including diagnostics and therapeutics and can be chemically synthesized using known techniques. Furthermore, aptamers can offer a number of advantages over traditional antibodies including avoiding the need to specifically know the precise epitopes or biomarkers themselves. Finally, aptamers are typically non-immunogenic, easy to synthesize, characterize, modify and exhibit high specificity and affinity for their target antigen.

By using a variety of selection techniques, aptamers can be selected to find targets, e.g., on a surface or inside a cell of interest, without the need to identify the precise biomarker or epitopes themselves. In many cases, the aptamer identification process can begin with a large random pool of oligonucleotides or peptides that are systematically subjected to negative and positive rounds of selection against a target, e.g., a protein molecule, to filter out low affinity or unspecific binders. The remaining aptamers can be collected and propagated, e.g., PCR amplified, and used in subsequent rounds of selection. This selection process, referred to as Systemic Evolution of Ligands by Exponential Enrichment or SELEX, is commonly used for selecting and identifying highly-targeted aptamers. A variant of this methodology, known as cell-SELEX, has been developed for aptamers which are capable of recognizing whole living cells.

Certain non-modified aptamers can have a rapid clearance rate from the body due to their small size and degradation by nucleases in vivo. In some instances, rapid clearance can be an advantage in application such as in vivo diagnostic imaging. However, the clearance rate can also be adjusted by chemical modification of the aptamers. Several approaches have been adopted to chemically optimize the properties of aptamers such as: (1) capping their terminal ends, (2) substituting naturally occurring nucleotides with unnatural nucleotides (i.e., 2'-F, 2'-OCH3 or 2'-NH2 modified nucleotides) which are poor substrates for nuclease degradation; (3) using unnatural internucleotide linkage groups (e.g., phosphorothioate linkages) can be used, (4) using altered sugar moieties, or (5) conjugating polymers such as PEG or lipids such as cholesterol to the aptamer to enhance aptamer lifetime during in vivo use. Alternatively, modified nucleotides containing altered base (such as 2'-fluorine-substituted pyrimidines, 2'-amino pyrimidines, and 2'-O-methyl ribose purines and pyrimidines), sugar, and internucleotide linkage groups (e.g., phosphorothioate linkages) can be used in the aptamer synthesis to increase nuclease resistance. The presence of these modified nucleotides stabilizes oligonucleotides against nuclease-mediated degradation and imparts greater affinities to selected aptamers. Another approach to increase nuclease resistance of aptamers is to develop "spiegelmers" which are composed entirely of unnatural L-ribonucleic acid backbone. Through combining some of these approaches, an aptamer's half-life can be prolonged from several minutes to many hours.

Representative methods for preparing and isolating aptamers that are specific for target analytes are described, for instance, in K. Sefah et al. *Nature Protocols*, Vol. 5, pp. 1169-1185 (June 2010) describing aptamers specific for any cell type and Q. Shen et al., *Adv. Mater.*, Vol. 25, pp. 2368-2373. DOI: 10.1002/adma.201300082, describing preparation of aptamers specific for A549 non-small cell lung cancer cells, which are incorporated by reference in their entirety. Aptamers are also available commercially. See, for instance, OTCbiotechnologies, LLC, San Antonio, Tex., USA and Base Pair Biotechnologies, Inc., Houston, Tex., USA; and AMS biotechnology (Europe) LTD, Abingdon, UK. In addition, catalytic aptamers or DNAzyme having enzymatic activity can be created de novo by in vitro selection under normal or demanding reaction conditions and these catalytic aptamers can be used in creating sensors based on the immobilization of the DNAzyme onto a suitable substrate. See Nutiu et al. Pure Appl. Chem. 2004, Vol. 76 (Nos. 7-8), pp. 1547-1561; and Tram et al, J. Nucleic Acids, 2012, Vol. 2012, Article 958683, pages 1-8, DOI: 10.1155/2012/958683, which are incorporated by reference in this entirety.

Aptamer conjugates can be used for detection and/or monitoring of a broad variety of target analytes in vivo. Clinically relevant target analytes can include any analyte that, when present in or absent from the interstitial fluid, or present at a particular concentration or range of concentrations, may be indicative of a medical condition or indicative that a medical condition may be imminent. For example, a clinically-relevant analyte could be an ion, enzyme, hormone, protein, or other molecule.

Representative examples of target analytes include, without limitation, serum glucose, calcium, blood urea nitrogen, creatinine, creatine kinase, sodium, potassium chloride, carbon dioxide, oxygen, serum calcium, serum total protein (TP), human serum albumin, bilirubin, alkaline phosphatase (ALP) aspartate amino transferase (AST), alanine amino transferase (ALT), glucose, urea, uric acid, and insulin. Additional representative target analytes include lactate, cardiac enzymes, pharmaceuticals, metabolites, drug metabolites, hormones, cytokines, growth factors, circulating nucleic acids, circulating peptides, circulating viruses, and circulating cells.

Aptamers may be labeled or conjugated with any suitable labeling moiety. A "labeling moiety" or "labels" as used herein, is intended to mean a chemical compound, molecule, ion, or particle that directly possesses or indirectly comes to possess a detectable signal. Particles may include microparticles and nanoparticles. The particles may be further labeled with other compounds or molecules such as fluorophores or auto-fluorescent or luminescent markers or non-optical contrast agents (e.g., acoustic impedance contrast, RF contrast and the like) or enzymes or enzyme substrates which may further assist in interrogating the aptamer conjugates in vivo. The labels used in the present invention may be used to indicate a conformational change of the aptamer which can be indicative of target binding. The labeling moieties used in the current methods and compositions can be attached through any suitable means including chemical means, such as reduction, oxidation, conjugation, and condensation reactions. For example, any thiol-reactive group can be used to attach labeling moieties, e.g., a fluorophore, to a naturally occurring or engineered thiol group present in the aptamer. Also, for example, reactive groups present in the aptamer can be labeled using succinimide ester derivatives of fluorophores. See Richieri, G. V. et al., J. Biol. Chem., 267: 23495-501 (1992) which is hereby incorporated by reference.

Alternatively, the aptamer can be coupled to a label, e.g., a particle such as a nanoparticle, using well-known click chemistry which entails labeling the aptamer with an azide or alkyne group and coupling the labeled aptamer to an alkyne/azide group on the particle. Alternatively, the aptamer may be labeled with an NH2 group and then coupled to —COOH group on the particle using 1-ethyl-3-[3-dimethylaminopropyl]carbodiimide hydrochloride (EDC or EDAC) cross-linking agent (commercially available from Thermo Fisher Scientific, Inc., Rockford, Ill., USA). In addition, photocleavable linkers or spacers can be used to conjugate the aptamer to a particle. Photocleavable linkers are commercially available. See for instance Integrated DNA Technologies, Inc., Coralville, Iowa., USA; and Ambergen, Inc., Watertown, Mass., USA).

In one embodiment, the labeling moiety can emit an optical signal. Numerous labels are known by those of skill in the art and include, but are not limited to, particles, fluorophores, haptens, enzymes and their colorimetric, fluorogenic and chemiluminescent substrates and other labels that are described in RICHARD P. HAUGLAND, MOLECULAR PROBES HANDBOOK OF FLUORESCENT PROBES AND RESEARCH PRODUCTS (9th edition, CD-ROM, (September 2002), which is herein incorporated by reference.

A fluorophore label can be any chemical moiety that exhibits an absorption maximum at or beyond 280 nm, and when covalently attached to the aptamer or other reagent retains its spectral properties. Fluorophores of the present invention include, without limitation; a pyrene (including any of the corresponding derivative compounds disclosed in U.S. Pat. No. 5,132,432, incorporated by reference), an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine, a carbocyanine (including any corresponding compounds in U.S. Pat. Nos. 4,981,977; 5,268,486; 5,569,587; 5,569,766; 5,486,616; 5,627,027; 5,808,044; 5,877,310; 6,002,003; 6,004,536; 6,008,373; 6,043,025; 6,127,134; 6,130,094; 6,133,445; 6,664,047; 6,974,873 and 6,977,305; and publications WO 02/26891, WO 97/40104, WO 99/51702, WO 01/21624; EP 1 065 250 A1, incorporated by reference), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896, incorporated by reference), a xanthene (including any corresponding compounds disclosed in U.S. Pat. Nos. 6,162,931; 6,130,101; 6,229,055; 6,339,392; 5,451,343 and 6,716,979, incorporated by reference), an oxazine (including any corresponding compounds disclosed in U.S. Pat. No. 4,714,763, incorporated by reference) or a benzoxazine, a carbazine (including any corresponding compounds disclosed in U.S. Pat. No. 4,810,636, incorporated by reference), a phenalenone, a coumarin (including an corresponding compounds disclosed in U.S. Pat. Nos. 5,696,157; 5,459,276; 5,501,980 and 5,830,912, incorporated by reference), a benzofuran (including an corresponding compounds disclosed in U.S. Pat. Nos. 4,603,209 and 4,849,362, incorporated by reference) and benzphenalenone (including any corresponding compounds disclosed in U.S. Pat. No. 4,812,409, incorporated by reference) and derivatives thereof. As used herein, oxazines include resorufins (including any corresponding compounds disclosed in U.S. Pat. No. 5,242,805, incorporated by reference), aminooxazinones, diaminooxazines, and their benzo-substituted analogs. When the fluorophore is a xanthene, the fluorophore is optionally a fluorescein, a rhodol (including any corresponding compounds disclosed in U.S. Pat. Nos. 5,227,487 and 5,442,045, incorporated by reference), or a rhodamine (including any corresponding compounds in U.S. Pat. Nos. 5,798,276; 5,846.737 and 6,562,632, incorporated by reference). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171, incorporated by reference). Alternatively, the fluorophore is a xanthene that is bound via a linkage that is a single covalent bond at the 9-position of the xanthene. Preferred xanthenes include derivatives of 3H-xanthen-6-ol-3-one attached at the 9-position, derivatives of 6-amino-3H-xanthen-3-one attached at the 9-position, or derivatives of 6-amino-3H-xanthen-3-imine attached at the 9-position.

Fluorophores for use in the present invention include, but are not limited to, xanthene (rhodol, rhodamine, fluorescein and derivatives thereof) coumarin, cyanine, pyrene, oxazine and borapolyazaindacene. Sulfonated xanthenes, fluorinated xanthenes, sulfonated coumarins, fluorinated coumarins and sulfonated cyanines are useful. The choice of the fluorophore will determine the absorption and fluorescence emission properties of the aptamer conjugate. Physical properties of a fluorophore label include spectral characteristics (absorption, emission and stokes shift), fluorescence intensity, lifetime, polarization and photo-bleaching rate all of which can be used to distinguish one fluorophore from another.

Typically the fluorophore contains one or more aromatic or heteroaromatic rings, that are optionally substituted one or more times by a variety of substituents, including without limitation, halogen, nitro, cyano, alkyl, perfluoroalkyl, alkoxy, alkenyl, alkynyl, cycloalkyl, arylalkyl, acyl, aryl or heteroaryl ring system, benzo, or other substituents typically present on fluorophores known in the art.

Specific examples of fluorophore labels are selected from the group consisting of fluorescein, coumarins, rhodamines, 5-TMRIA (tetramethylrhodamine-5-iodoacetamide), (9-(2 (or 4)-(N-(2-maleimdylethyl)-sulfonamidyl)-4 (or 2)-sulfophenyl)-2,3,6,7,12,13,16,17-octahydro-(1-H,5H,11H,15H-xantheno(2,-3,4-ij:5,6,7-i'j')diquinolizin-18-ium salt) (TEXAS RED), 2-(5-(1-(6-(N-(2-maleimdylethyl)-amino)-6-oxohexyl)-1,3-dihydro-3,3-dimet-hyl-5-sulfo-2H-indol-2-ylidene)-1,3-propyldienyl)-1-ethyl-3,3-dimethyl-5-s-ulfo-3H-indolium salt (Cy3), N,N'-dimethyl-N-(iodoacetyl)-N'-(7-nitrobenz-2-oxa-1,3-diazol-4-yl)ethyle-nediamine (IANBD amide), N-((2-(iodoacetoxy)ethyl)-N-methyl) amino-7-nitrobenz-2-oxa-1,3-diazole (IANBD ester), 6-acryloyl-2-dimethylaminonaphthalene (acrylodan), pyrene, 6-amino-2,3-dihydro-2-(2-((iodoacetyl)amino) ethyl)-1,3-dioxo-1H-benz(de)i-soquinoline-5,8-disulfonic acid salt (lucifer yellow), 2-(5-(1-(6-(N-(2-maleimdylethyl)-amino)-6-oxohexyl)-1,3-dihydro-3,3-dimet-hyl-5-sulfo-2H-indol-2-ylidene)-1,3-pentadienyl)-1-ethyl-3,3-dimethyl-5-su-lfo-3H-indolium salt (Cy™5), 4-(5-(4-dimethylaminophenyl)oxazol-2-yl)phenyl-N-(2-bromoacetamidoethyl)sulfonamide (Dapoxyl®(2-bromoacetamidoethyl)sulfonamide)), (N-(4,4-difluoro-1,3,5,7-tetramethyl-4-bora-3a,4a-diaza-s-indacene-2-yl)i-odoacetamide (BODIPY 507/545 IA), N-(4,4-difluoro-5,7-diphenyl-4-bora-3a,4a-diaza-s-indacene-3-propionyl)-N-'-iodoacetylethylene diamine (BODIPY 530/550 IA), 5-((((2-iodoacetyl)amino)ethyl)amino)napthalene-1-sulfonic acid (1,5-IAEDANS), and carboxy-X-rhodamine, 5/6-iodoacetamide (XRIA 5,6). Another example of a label is BODIPY-FL-hydrazide. Other luminescent labels include lanthanides such as europium (Eu3+) and terbium (Tb3+), as well as metal-ligand complexes of ruthenium [Ru(II)], rhenium [Re(I)], or osmium [Os(II)], typically in complexes with diimine ligands such as phenanthroline.

Binding of the aptamer conjugates to a target analyte may be detected with or without an interrogation signal input. The term "binding" is understood in its broadest sense to include any detectable interaction between the aptamer and the target analyte. For example, some conjugates may be functionalized with compounds or molecules, such as fluorophores or autofluorescent, luminescent or chemiluminescent markers, which generate a responsive signal when the conjugates bind to the target analyte without the input of a stimulus. In other examples, the aptamer conjugates may produce a different responsive signal in their bound versus unbound state in response to an external stimulus, such as an electromagnetic, acoustic, optical, or mechanical energy.

Suitable optical signals which can be used as an assay readout include any optical signal which can be generated by a proximity assay, such as those generated by fluorescence resonance energy transfer (FRET), fluorescence polarisation, fluorescence quenching, phosphorescence technique, luminescence enhancement, luminescence quenching, diffraction or plasmon resonance, all of which are known techniques.

In one embodiment, the substrate incorporates assay components which generates an optical readout using FRET. In this assay format, a pair of fluorophores are used wherein one serves as a donor chromophore and the other acts as an acceptor chromophore, With respect to the fluorescence emission spectrum, the emission spectrum of donor chromophore overlaps with the absorption spectrum of acceptor chromophore, such that when the donor and acceptor chromophores are brought into close proximity, a proportion of the energy which normally would produce fluorescence emitted by the donor chromophore (following irradiation with incident radiation of a wavelength absorbed by the donor chromophore) will be non radiatively transferred to the adjacent acceptor chromophore, a process known in the art as fluorescence resonance energy transfer, with the result that a proportion of the fluorescent signal emitted by the donor chromophore is quenched, that the lifetime of the fluorescence is changed, and, in some instances, that the acceptor chromophore emits fluorescence. The acceptor chromophore may, however, be a non-fluorescent dye. Fluorescence resonance energy transfer generally only occurs when the donor and acceptor chromophores are brought into close proximity by the binding of, for instance, the binding of an analyte to an aptamer which causes a conformation change which brings the donor and acceptable chromophores together. Thus, in the presence of analyte, the amount of quenching is reduced (resulting in a measurable increase in the intensity of the fluorescent signal emitted by the donor chromophore or a fall in the intensity of the signal emitted by the acceptor chromophore). The intensity or lifetime of the fluorescent signal emitted from the donor chromophore thus correlates with the concentration of target analyte in the interstitial fluid bathing the sensor.

An additional advantageous feature of the FRET assay format arises from the fact that any fluorescent signal emitted by the acceptor chromophore following excitation with a beam of incident radiation at a wavelength within the absorption spectrum of the acceptor chromophore is unaffected by the FRET process. It is therefore possible to use the intensity of the fluorescent signal emitted by the acceptor chromophore as an internal reference signal, for example in continuous calibration of the sensor or to monitor the extent to which the sensor has degraded and thus indicate the need to implant or inject a fresh sensor. As the biodegradable material degrades, the amount of acceptor chromophore present in the sensor will decrease, and hence the intensity of fluorescent signal detected upon excitation of the acceptor chromophore will also decrease. The fall of this signal below an acceptable baseline level would indicate the need to implant or inject a fresh sensor. Competitive binding assays using the FRET technique are known in the art. See for instance, U.S. Pat. No. 3,996,345 describes immunoassays employing antibodies and fluorescence resonance energy transfer between a fluorescer-quencher chromophoric pair; Meadows and Schultz (Anal. Chim. Acta (1993 280: pp 21-30) describe a homogeneous assay method for the measurement of glucose based on FRET between a labelled glucose analog (FITC labelled dextran) and a labelled glucose binding agent (rhodamine labelled concanavalin A), all which are incorporated by reference herein. Any suitable configurations of acceptor and donor chromophores/quenchers can be employed herein.

The sensor can be adapted for the detection or quantitative measurement of any target analyte present in interstitial fluid such as glucose (in connection with the long-term monitoring of diabetics), urea (in connection with kidney disease or dysfunction), lactate (in connection with assessment of muscle performance in sports medicine), ions such as sodium, calcium or potassium and therapeutic drugs whose concentration in the blood must be closely monitored, such as, for example, digoxin, theophylline or immunosuppressant drugs. The above analytes are listed by way of example only and it is to be understood that the precise nature of the analyte to be measured is not material.

The sensor can be interrogated transcutaneously using optical means i.e. no physical connection is required between the sensor and the optical means. When the sensor incorporates the technique of fluorescent energy transfer, the optical means can supply a first beam of incident radiation at a wavelength within the absorption spectrum of the donor chromophore and a second beam of incident radiation at a wavelength within the adsorption spectrum of the acceptor chromophore. In addition, the optical means can be capable of measuring optical signals generated in the sensor at two different wavelengths; wavelength 1 within the emission spectrum of the donor chromophore (the signal generated in connection with the measurement of analyte and wavelength 2 in the emission spectrum of the acceptor chromophore (which could be the analyte signal or the internal reference or calibration signal).

Optical means suitable for use in remote interrogation of the sensor can include a simple high-throughput fluorimeter comprising an excitation light source such as, for example, a light-emitting diode (blue, green or red), an excitation light filter (dichroic or dye filter) and a fluorescent light detector (PIN diode configuration). A fluorimeter with these characteristics may exhibit a sensitivity of between picomolar to femtomolar fluorophore concentration.

Figure 3A:
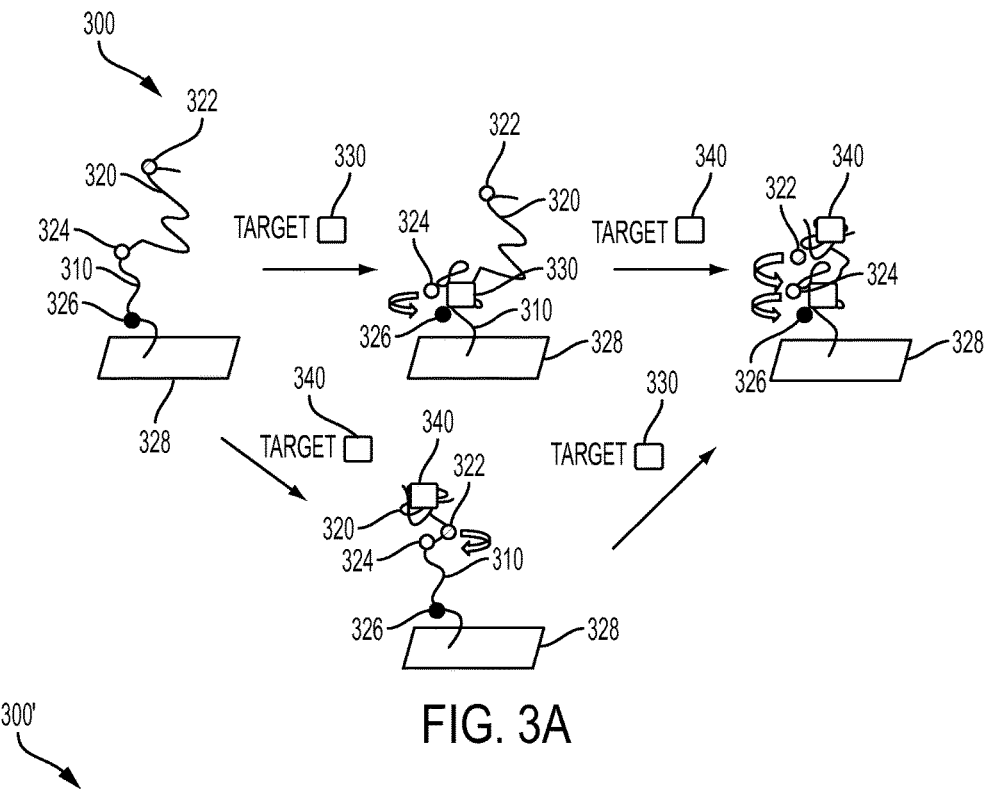
FIG. 3A is an example assay involving a substrate with a sensor having two aptamers coupled together with three different fluorescent dyes in the presence of one or two target analytes.

As shown in FIG. 3A, an example of sensor geometry 300 for coupled readout of two components is provided. Here, two aptamer conjugates 310 and 320 bound to a substrate 328 or a component of the substrate are coupled together with three different fluorescent dyes 322, 324, and 326 on the substrate. Upon binding of a first target 330 or a second target 340, the aptamer conjugates 310 and 320 undergo a conformational change to produce a unique FRET signal. In the presence of both targets 330 and 340, both aptamer conjugates 310 and 320 will fold to produce a multi-color FRET.

Figure 3B:
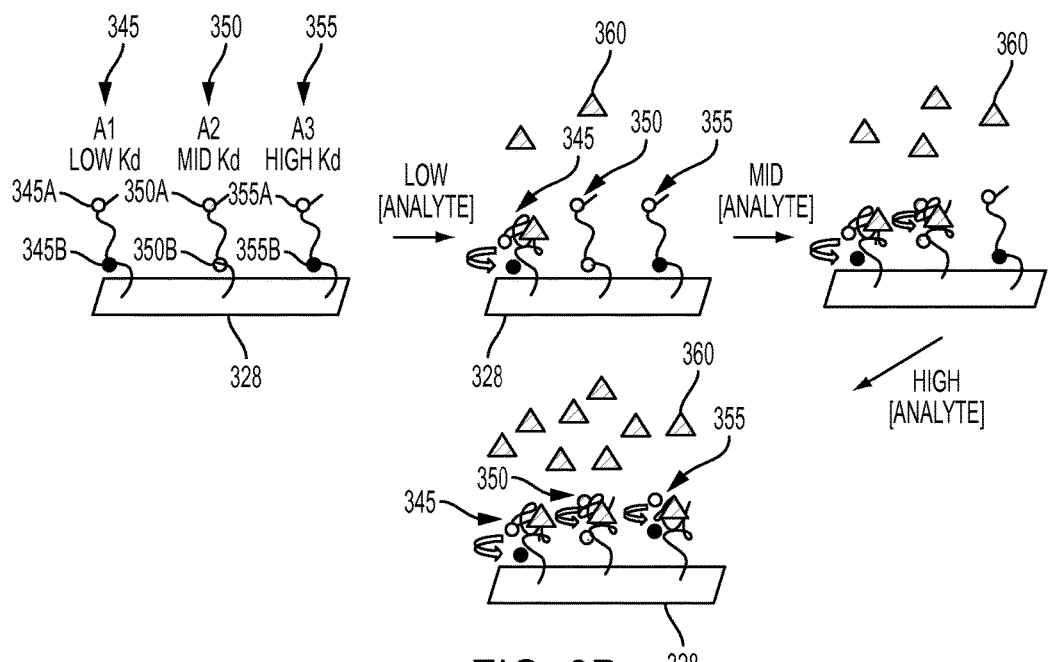
FIG. 3B is an example assay involving a substrate with a sensor having three different types of aptamers for the same target analyte.

FIG. 3B provides another example of sensor geometry 300' for a multiplexed/gradiometric readout. Three different types of aptamer conjugates 345, 350, and 355 bound to a substrate 328 or component of the substrate, each with a different binding constant (Kd) for the same target analyte 360 and each are functionalized with different FRET donor/acceptor pair 345A/345B, 350A/350B, and 355A/355B, respectively. In low levels of target analyte 360, the aptamer conjugate 345 with the smallest Kd binds and produces a distinct FRET signal. As the analyte level increases, the aptamer conjugate 350 with the next highest Kd value binds and produces a FRET signal. At high analyte levels, all the aptamer conjugates 345, 350 and 355 are bound to the target analyte 360 and all produce a FRET signal. The level or concentration of analyte 360 can be determined by either the combination of different FRET signals present if they are all different for each aptamer type or the cumulative signal if the FRET signals are the same for all the aptamer types.

In one embodiment, multiple analyte detection is possible. By immobilizing a plurality of aptamers of different binding specificity to target analytes, each aptamer distinctly labeled, e.g., different fluorophores, simultaneous multiple target analyte determinations can be made, thereby providing clinicians with deeper insight into the identification and assessment of health state and disease progression. The use of spectral filters and/or alternative light sources as the interrogation signal can be used to excite the label, e.g., fluorophores and detect light, e.g., fluorescent light, from the different labels, and thereby, determine the contribution of each fluorophore to the total fluorescent properties of the sample.

ii. Polymers

In one embodiment, the aptamers can be entrapped, immobilized, or encapsulated by physical or chemical means on or within the polymer matrix. Any suitable polymer may be used such as smart polymers or stimuli-response polymers, including hydrogels. As used herein, the term "entrap" and variations thereof is used interchangeably with "encapsulate" and is used to mean that the aptamer is immobilized within or on the constituents of the matrix. As used herein, "matrix" refers to essentially a three-dimensional environment which has at least one aptamer immobilized therein for the purpose of measuring a detectable signal from analyte-aptamer interaction. The relationship between the constituents of the matrix and the aptamers, include, but are not limited to, covalent, ionic, and Van der Wals interactions and combinations thereof. The spatial relationship between the matrix and the aptamers includes heterogeneous and homogeneous distribution within and or upon any or all of the matrix volume. The polymer matrix may be comprised of organic material, inorganic material, glass, metal, plastic, or combinations thereof.

The polymer matrix can be in any desirable form or shape including one or more of disk, fiber, cylinder, patch, nanoparticle, microsphere, porous polymer, open cell foam, and combinations thereof providing it permits permeability to analyze. The polymer matrix additionally prevents leaching of the aptamer from the sensing mechanism. The polymer matrix permits light from optical sources or any other interrogating signals to or from the reporter group bound to the aptamer to pass through the biosensor. When used in an in vivo application, the biosensor will be exposed to a substantially physiological range of analyte and determination or detection of a change in analyte concentration would be desired whereas the determination or detection includes continuous, programmed, and episodic detection means.

The polymer matrix may be prepared from biocompatible materials or incorporates materials capable of minimizing adverse reactions with the body. Adverse reactions for implants include inflammation, protein fouling, tissue necrosis, immune response and leaching of toxic materials. Such materials or treatments are well known and practiced in the art, for example as taught by Quinn, C. P.; Pathak, C. P.; Heller, A.; Hubbell, J. A. Biomaterials 1995, 16(5), 389-396, and Quinn, C. A. P.; Connor, R. E.; Heller, A. Biomaterials 1997, 18(24), 1665-1670, which are incorporated by reference in their entirety.

Hydrogels as polymers are particularly useful. As used herein, the term "hydrogel" is used to indicate a water-insoluble, water-containing polymer networks. Numerous hydrogels may be used in the present invention. The hydrogels may be, for example, polysaccharides such as agarose, dextran, carrageenan, alginic acid, starch, cellulose, or derivatives of these such as, e.g., carboxymethyl derivatives, or a water-swellable organic polymer such as, e.g., polyvinyl alcohol, polyacrylic acid, polyacrylamide, polyethylene glycol, copolymers of styrene and maleic anhydride, copolymers of vinyl ether and maleic anhydride and derivates thereof. Derivatives providing for covalently crosslinked networks are preferred. Synthesis and biomedical and pharmaceutical applications of hydrogels have been described by a number of researchers. (See, e.g. "Biosensors Fundamentals and Applications", edited by A. D. F. Turner, I. Karube and G. S. Wilson; published from Oxford University Press, in 1988, incorporated by reference in its entirety). An exemplary hydrogel matrix derived from a water-soluble, UV crosslinkable polymer comprises poly(vinyl alcohol),N-methyl-4(4'-formylstyryl)pyridinium methosulphate acetal (CAS Reg. No. [107845-59-0]) available from PolyScience Warrington, Pa.

The polymers that are to be used in the hydrogel matrices may be functionalized. That is, the polymers or monomers comprising the polymers can possess reactive groups such that the hydrogel matrices are amenable to chemical reactions, e.g., covalent attachment. As used herein and throughout, a "reactive group" is a chemical group that can chemically react with a second group. The reactive group of the polymer or monomers comprising the polymer may itself be an entire chemical entity or it may be a portion of an entire chemical entity, including, but not limited to, single atoms or ions. Further, the second group with which the reactive group is capable of reacting can be the same or different from the reactive group of the polymer or monomers comprising the polymers. Examples of reactive groups include, but are not limited to, halogens, amines, amides, aldehydes, acrylates, vinyls, hydroxyls and carboxyls. In one embodiment, the polymers or monomers comprising the polymers of the hydrogel should be functionalized with carboxylic acid, sulfate, hydroxy or amine groups. In another embodiment of the present invention, the polymers or monomers comprising the polymers of the hydrogel are functionalized with one or more acrylate groups. In one particular embodiment, the acrylate functional groups are terminal groups. The reactive groups of the polymers or monomers comprising the polymers of the matrix may be reactive with any component of the matrix portion of the biosensor, such as, but not limited to, another polymer or monomer within the matrix, a binding protein and an additive.

Suitable polymers which may be used in the present invention include, but are not limited to, one or more of the polymers selected from the group consisting of poly(vinyl alcohol), polyacrylamide, poly (N-vinyl pyrolidone), poly (ethylene oxide) (PEO), hydrolysed polyacrylonitrile, polyacrylic acid, polymethacrylic acid, poly(hydroxyethyl methacrylate), polyurethane polyethylene amine, poly(ethylene glycol) (PEG), cellulose, cellulose acetate, carboxy methyl cellulose, alginic acid, pectinic acid, hyaluronic acid, heparin, heparin sulfate, chitosan, carboxymethyl chitosan, chitin, collagen, pullulan, gellan, xanthan, carboxymethyl dextran, chondroitin sulfate, cationic guar, cationic starch as well as salts and esters thereof. The polymers of the hydrogel matrix may also comprise polymers of two or more distinct monomers. Monomers used to create copolymers for use in the matrices include, but are not limited to acrylate, methacrylate, methyl methacrylate, methacrylic acid, alkylacrylates, phenylacrylate, hydroxyalkylacrylates, hydroxyalkylmethacrylates, aminoalkylacrylates, aminoalkylmethacrylates, alkyl quaternary salts of aminoalkylacrylamides, alkyl quaternary salts of aminoalkylmethacrylamides, and combinations thereof. Polymer components of the matrix may, of course, include blends of other polymers.

In one embodiment, the hydrogel is comprised of poly(ethylene glycol) dimethacrylate (PEGDMA). PEGDMA is commercially available in a variety of molecular weights. For example. PEGDMA is available from at least Aldrich Chemical Co. (Milwaukee, Wis. USA) and from Polysciences, Inc. (Warrington, Pa., USA) and can be synthesized in an assortment of molecular weights. In one embodiment, the molecular weight of PEGDMA used in the hydrogels of the present invention is from about 400 to about 4000. In a more specific embodiment, the molecular weight of the PEGDMA in the hydrogels is about 1000.

In another embodiment, the hydrogels comprise PEGDMA and at least one acrylate. As used herein, the term acrylate is well understood in the art. Specifically, acrylates are compounds, including but not limited to polymers, comprising the acrylic group ($HC2=CH-C(=O)$). Examples of acrylates include, but are not limited to, acrylic acid, ethyl acrylate, methacrylic acid, methyl methacrylic acid and acrylamides. In another specific embodiment, the hydrogels comprise more than one acrylate. In a more specific embodiment, the hydrogels comprise a mixture of methacrylate and methyl methacrylate.

The polymers used in the hydrogel matrices can be modified to contain nucleophilic or electrophilic groups. Indeed, the polymers used in the present invention may further comprise polyfunctional small molecules that do not contain repeating monomer units but are polyfunctional, i.e., containing two or more nucleophilic or electrophilic functional groups. These polyfunctional groups may readily be incorporated into conventional polymers by multiple covalent bond-forming reactions. For example, PEG can be modified to contain one or more amino groups to provide a nucleophilic group. Examples of other polymers that contain one or more nucleophilic groups include, but are not limited to, polyamines such as ethylenediamine, tetramethylenediamine, pentamethylenediamine, hexamethylenediamine, bis-(2-hydroxyethyl)amine, bis-(2-aminoethyl)amine, and tris-(2-aminoethyl)amine. Examples of electrophilic groups include but are not limited to, succinimide esters, epoxides, hydroxybenzotriazole esters oxycarbonylimidazoles, nitrophenyl carbonates, tresylates, mesylates, tosylates, carboxylates, and isocyanates. In one embodiment, the composition comprises a bis-amine-terminated poly(ethylene glycol.

The polymers should be capable of crosslinking, either physically or chemically, to form a hydrogel. Physical crosslinking includes, but is not limited to, such non-chemical processes as radiation treatment such as electron beams, gamma rays, x-rays, ultraviolet light, anionic and cationic treatments. The crosslinking of the polymers may also comprise chemical crosslinking, such as covalent crosslinking. For example, a chemical crosslinking system may include, but is not limited to, the use of enzymes, which is well-known in the art. Another example of the chemical covalent crosslinking comprises the use of peroxide. Chemical crosslinking may occur when a crosslinking reagent reacts with at least two portions of a polymer to create a three-dimensional network. Covalent crosslinking may also occur when multifunctional monomers are used during the crosslinking process. For example, an acrylate monomer may be polymerized with a bifunctional acrylate monomer to form a crosslinked polymer. Any crosslinking reagent will be suitable for the present invention, provided the crosslinking reagent will at least partially dissolve in water or an organic solvent and can form the crosslinked polymer. For example, if the polymer is an amine-terminated PEG, the crosslinking reagent should be capable of reacting with the PEG-amine groups and be substantially soluble in water. In another example, (hydroxyethyl methacrylate) and methacrylic acid monomers can be polymerized with poly(ethylene glycol)-bis-alkylacrylate crosslinking agent in water or in dimethylformide to form polymeric hydrogels.

If the polymers to be crosslinked are functionalized with nucleophilic groups, such as amines (primary, secondary and tertiary), thiols, thioethers, esters, nitrites, and the like, the crosslinking reagent can be a molecule containing an electrophilic group. Examples of electrophilic groups have been described herein. Likewise, if polymers to be crosslinked are functionalized with electrophilic groups, the crosslinking reagent can be a molecule containing a nucleophilic group. It is understood that one skilled in the art can exchange the nucleophilic and electrophilic functional groups as described above without deviating from the scope of the present embodiment. It is also understood that the binding molecule can provide the requisite nucleophilic and electrophilic functional groups. For example, where the binding molecule is a protein, the nucleophilic and electrophilic functional groups may be present as naturally occurring amino acids in the protein, or may be introduced to the protein using chemical techniques described herein. Other general methods for preparing or crosslinking polymers to form hydrogel matrices are well known in the art. For example, Ghandehari H., et al., J. Macromol. Chem. Phys. 197: 965 (1996); and Ishihara K, et al., Polymer J., 16: 625 (1984), all of which are hereby incorporated by reference, report the formation of hydrogels. Hydrogel matrix can be applied to each sensor tip, e.g. a needle, and cured under a Hg lamp, with wavelength of >360 nm, for about 15 seconds.

In one embodiment of the present invention, the aptamers are covalently attached to, i.e., entrapped within a hydrogel. The covalent attachment of the aptamers to the hydrogel should not interfere with the binding of the aptamer to the target ligand. Furthermore, the covalent attachment of the aptamer to the hydrogel should be resistant to degradation. The functional group in one embodiment, a polymer or other component of the hydrogel serves to couple the aptamer to the hydrogel. The coupling of the aptamer to the hydrogel can be accomplished in any number of ways. For example, coupling reactions between the hydrogel and binding molecule include, but are not limited to, diazonium coupling, isothiocyano coupling, hydrazide coupling, amide formation, disulfide coupling, maleic anhydride coupling, thiolactone coupling, and dichlotriazine coupling. These coupling reactions between two functional groups are well documented, and are considered well known to those skilled in the art. For example, an amino functional group in an aptamer can be covalently coupled to a carboxyl functional group of one or more components of a hydrogel using coupling agents such as 1-ethyl-3-(3-dimethylaminopropyl) carbodiimide hydrochloride (EDC) or dicyclohexylcarbodiimide (DCC). It is understood that the amino and carboxyl functional groups of the binding molecule and one or more components of the hydrogel as described above can be transposed without deviating from the scope of the embodiment.

In another embodiment, the aptamers may be bound encapsulated non-covalently within polymer matrix or scaffold by any suitable means that allows analyte-induced conformational change of the aptamers, retension of the aptamers within the polymer to prevent loss or leaching of the aptamer, and to provide a stable, continuous and reversible sensor response to changing concentrations of the target analyte of interest. For instance, well-established processes for enzyme immobilization in hydrogels may be used.

In one embodiment, the substrate can be made of a biodegradable material or polymer. In another embodiment, the substrate can be coated or embedded within a matrix of biodegradable material or polymer. In some embodiments, the substrate can be retained by an envelope of biodegradable material or polymer, or may be separately covered with biodegradable material or polymer.

Materials suitable as biodegradable materials for the substrate include biodegradable block copolymers such as those described by Jeong et al., Nature 388: pp 860-862, incorporated by reference in its entirety. Aqueous solutions of these materials are thermosensitive, exhibiting temperature-dependent reversible gel-sol transitions. In one embodiment, the substrate is coated with the polymer biodegradable material at an elevated temperature where the material forms a sot. In this form the material is injectable and on cutaneous injection and subsequent rapid cooling to body temperature the material forms a gel matrix. The substrate is suspended within this gel matrix which thus constitutes a sensor suitable for detecting or measuring analytes in interstitial fluid. Low molecular weight analytes, such as glucose, can freely diffuse into the gel matrix from the surrounding interstitial fluid. Cutaneous injection of the sol phase material causes neither significant pain or tissue damage in the patient.

Alternatively, the substrate can be made from a solid or gel-like polymer biodegradable material within which the sensor components are mounted or distributed. When injected or implanted cutaneously this solid polymer sensor hydrates and swells, and target analyte penetrates through the structure to encounter the substrate.

Biodegradable materials suitable for use in the coating of the substrate or the construction of the substrate include cross-linked proteins such as human albumin, fibrin gels, polysaccharides such as starch or agarose, polylactides (PLA) such as poly (DL-lactide), polyglycolides (PGA) such as poly (DL-glycolide), poly(lactide-co-glycolides) (PLGA), polyanhydrides, polyorthoesters, fatty acid/cholesterol mixtures that form semi-solid derivates, hyaluronates and liquid crystals of monoolein and water. These materials have the advantage that they are broken down into biologically acceptable molecules which are metabolised and removed from the body via normal pathways.

In some embodiments, it is advantageous for the assay components to have a restricted diffusion in order to minimise their loss from the substrates into the bloodstream. This can be achieved by ensuring that the biodegradable material has a pore size that permits the diffusion of low molecular weight analytes such as glucose, but not diffusion of the assay components themselves. The assay components are preferably of high molecular weight, such as proteins or polymers, in order to restrict their loss from the sensor.

IV. Methods for Implantation

The dimensions of the substrate can vary as desired as described above. In one embodiment, the substrate can be directly injected into the skin using a suitable injection device such as a syringe having a narrow bore hypodermic needle. Because the substrate including the sensor does not itself contain any of the optical components required to interrogate the readout of the assay (these being provided separately and located outside the body) the sensor can easily be provided in any suitable shape, form or size which is injectable into the skin with minimal discomfort to the patient.

The substrate may be introduced within the skin by injection, using a syringe or by other methods such as the methods described in WO00/02048 which is incorporated by reference in its entirety. The substrate may be introduced within the thickness of the dermis, or sub-dermally, or may be introduced to the epidermis, although in the tatter case it would be likely to be expelled from the skin by outgrowth of the epidermal layers, possibly before the biodegradable material, if present, has degraded.

Because the substrate is located within the skin, an optical generated in the sensor can be detected transcutaneously (i.e. through the higher layer(s) of the skin) thus obviating the need for any direct connection between the sensor and the external environment. Once the substrate is in place in a cutaneous location, analyte measurements can be taken as often as is necessary with no adverse effects. This can be an advantage in relation to the long-term care of diabetic patients because if glucose measurements are taken more frequently, tighter control can be maintained over the level of glucose in the blood and the risk of developing conditions related to poorly regulated blood glucose, such as retinopathy, nephropathy, neuropathy, general micro- and macrovascular damage and poor circulation can be reduced.

The biodegradable material if present and substrate can be permeable to interstitial fluid, thereby allowing analytes such as glucose to enter the substrate by diffusion and to interact with the components of the assay.

The biodegradable material may be an injectable formulation that forms a get at the point of injection within the skin of the patient. The substrate may be formed from a solid polymeric material incorporating the components of the assay which is again injected or implanted cutaneously, the polymeric material typically being of a size suitable for injection through a narrow gauge needle to minimize the discomfort to the patient. When placed cutaneously, the solid polymeric material absorbs water and expands to form a gel, thus hydrating the components of the assay.

The biodegradable material may contain the substrate such that it is held in position at the site of injection. This enables optical measurements to be taken at the skin surface over this position. The assay contained in the substrate can thus be interrogated simultaneously to give a measurable signal.

The biodegradable material, if present, can degrade over a period of time within the skin, releasing the substrate. At this point the useful lifetime of the sensor is over, and it is desirable to remove the substrate and/or sensor from the body. Alternatively, if non-biodegradable material is used, the substrate can be removed from the body at any time once it is no longer needed. If the substrate and/or sensor are to be removed from the body, it can be simply removed using a syringe to aspirate the substrate. Non-invasive imaging methods such as high frequency ultrasound and optical coherence tomography that provide real-time feedback on the relative position of the needle and substrate can be used.

Figure 4A:
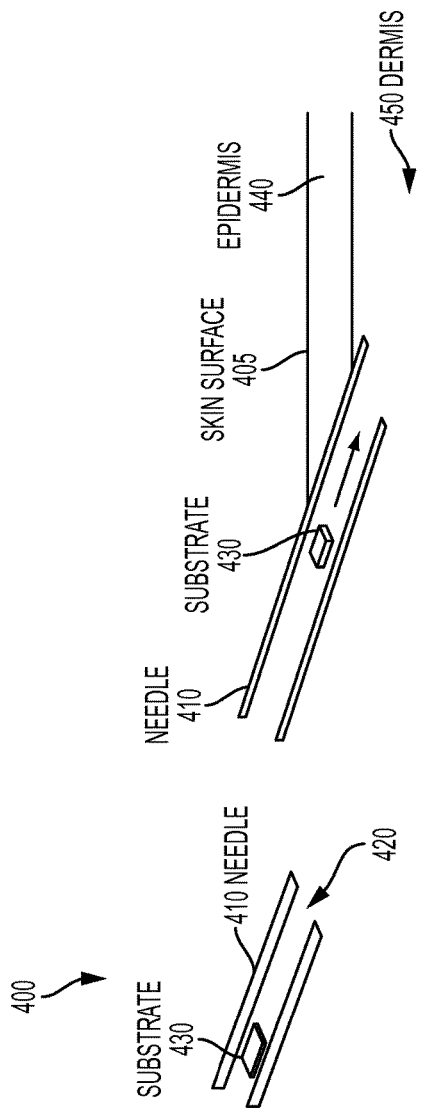
FIG. 4A is a side cross-section view enhanced to show an example substrate being implanted via injection into the dermal layer of the skin of an arm.

FIG. 4A illustrates a cross-sectional view 400 expanded to show an example implantation of a substrate underneath the surface of skin 405. A hypodermic needle 410 having a hollow bore 420 including the substrate 430 in a fluid carrier is inserted. Any suitable fluid carrier for the substrate can be used including, for instance, water, saline solution, or aqueous liquid polymeric solution that forms a gel when injected into the skin as discussed above. The substrate is implanted past the epidermal layer 440 into the dermal layer 450 of the skin 405.

Figure 4B:
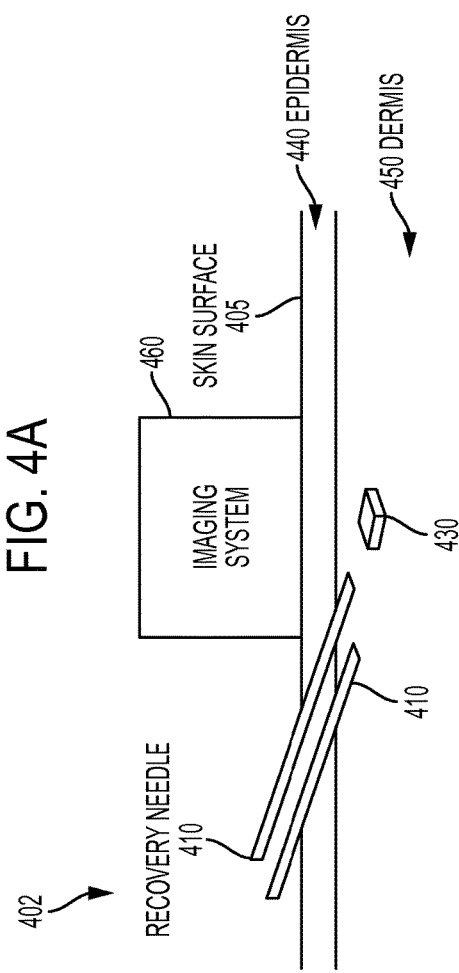
FIG. 4B is a side cross-section view enhanced to show the removal of a substrate from the dermal layer of the skin of an arm using needle aspiration guided by an imaging system.

FIG. 4B includes a cross-sectional view 402 expanded to show an example removal of a substrate 430 implanted beneath the surface of skin 405 using a hypodermic needle 410 to aspirate the implanted substrate 430 into its hollow bore 420. In this example, the needle is guided past the epidermal layer 405 into the dermal layer 440 using a real-time imaging system 460. Non-invasive imaging systems include high frequency ultrasound and optical coherence tomography which provide real-time feedback on the relative position of the needle and substrate.

IV. Example Optical Sensor

Figure 5A:
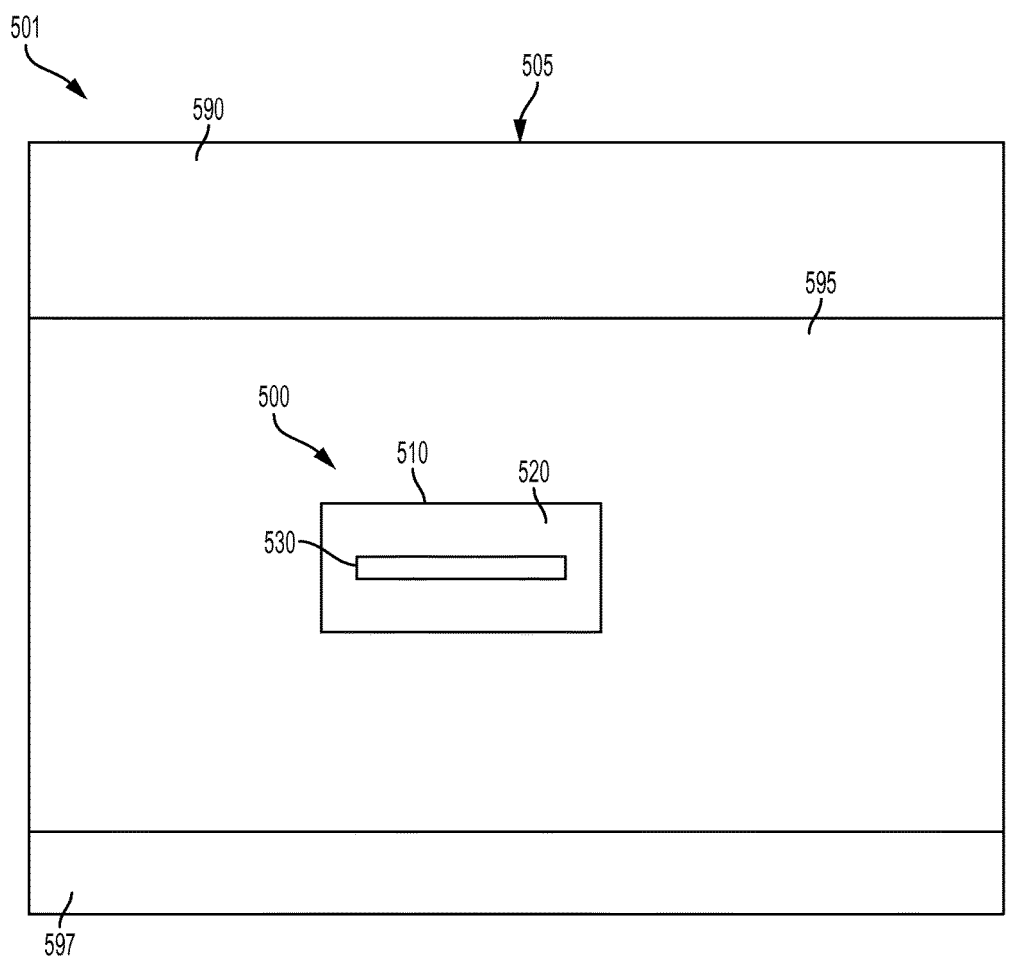
FIG. 5A is a side cross-section view of an example substrate while implanted into a layer of the skin of an arm.
Figure 5B:
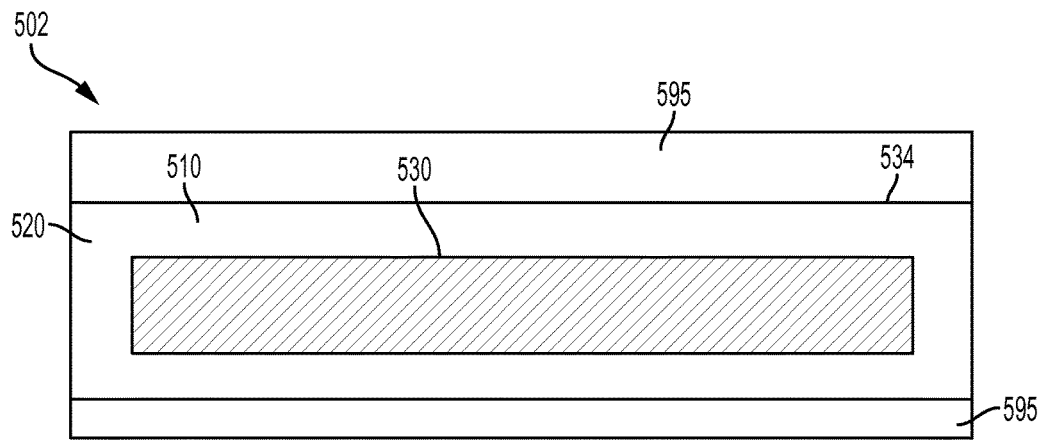
FIG. 5B is a side cross-section view enhanced to show the assay component of the example substrate when implanted as shown in FIG. 5A.
Figure 5C:
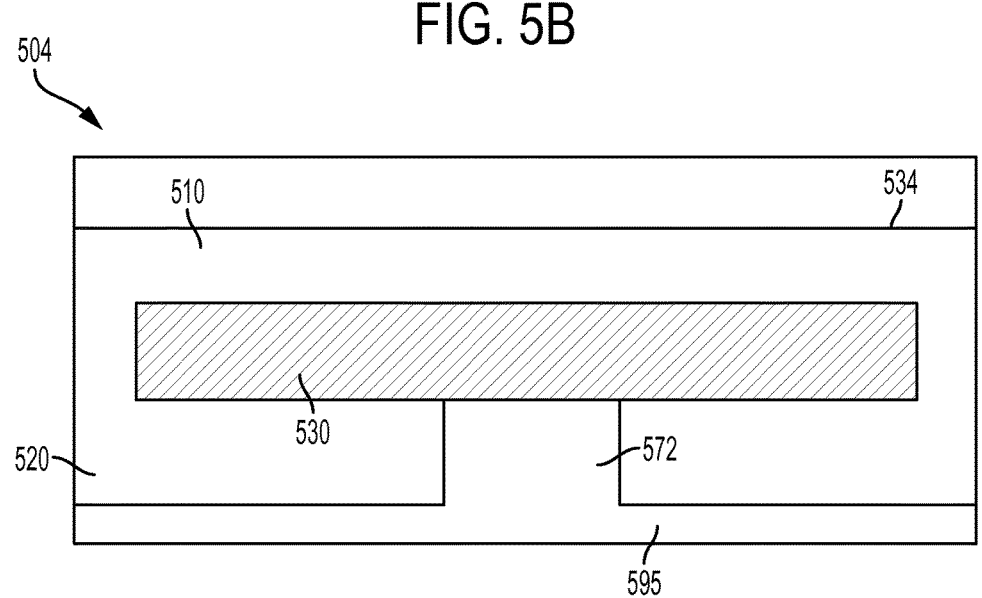
FIG. 5C is a side cross-section view enhanced to show the assay component and channel of the example substrate when implanted.

As shown in the cross-sectional views 501, 502 and 504 in FIGS. 5A, 5B and 5C, the substrate 510 can be implanted under the skin 505 which includes an epidermal layer 590, dermis 595, and subcutaneous fat layer 597. It is noted that relative dimensions in FIG. 5A are not necessarily to scale, but have been rendered for purposes of explanation only in describing the arrangement of the example implantable substrate 510. In the example shown, the substrate 510 implanted in the dermal layer 595 of skin can have a labeled aptamer conjugate as assay component 530 configured to undergo an optically-detectable change upon interaction with an analyte. In some examples, the optically-detectable change may involve a change in optical absorption, reflectivity, and/or fluorescence. The assay component 530 may be embedded in a polymeric material 520.

As shown in FIG. 5B, the assay component 530 may be embedded into the dermal layer 595 of skin. In some examples, the assay component 330 may penetrate into the skin so as to contact interstitial fluid. In this way, the assay component 330 can directly interact with an analyte in the dermal interstitial fluid which enters substrate 510 through channel 572.

V. Example Substrate/Reader Interactions

Figure 6A:
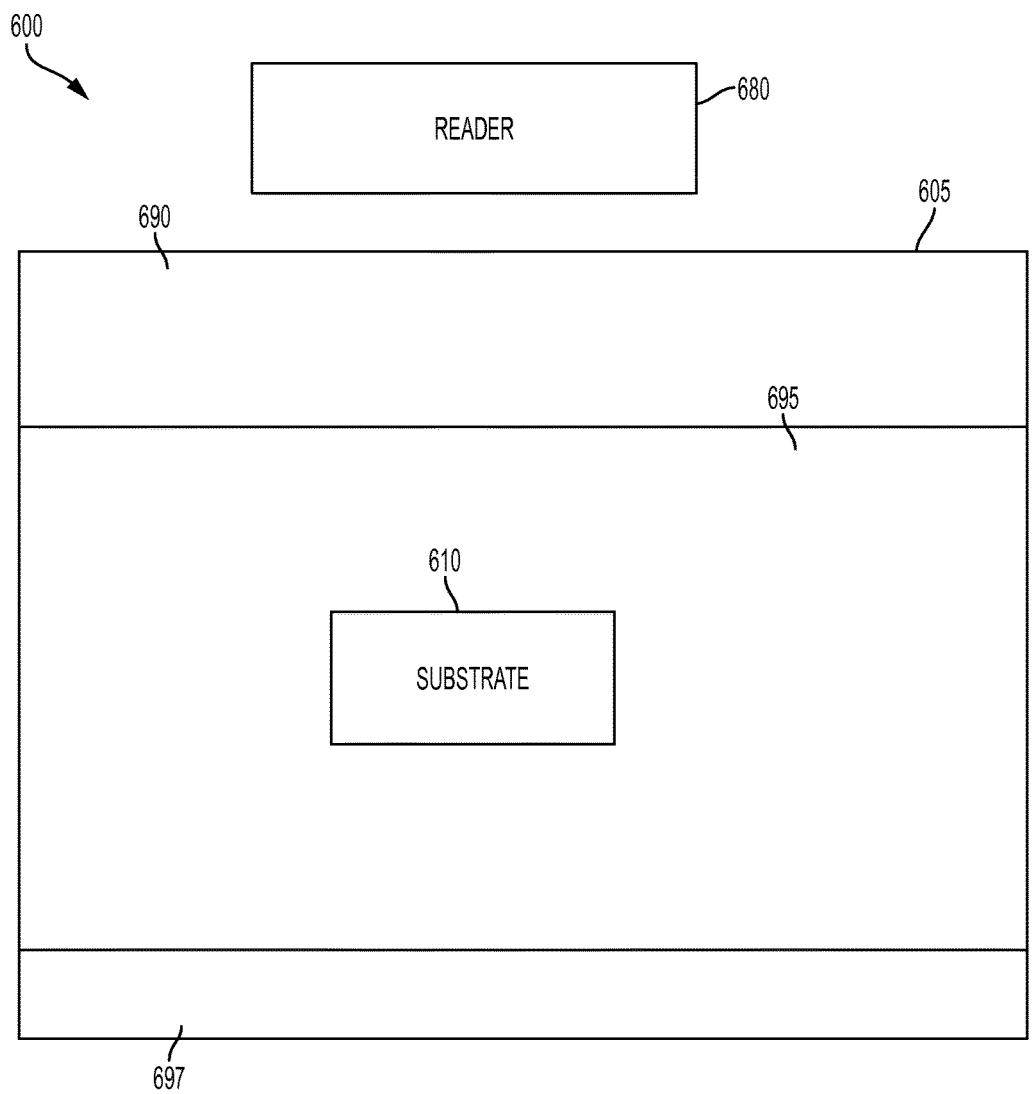
FIG. 6A is an example system that includes an implanted substrate and a proximate reader, in accordance with an example embodiment.

FIG. 6A is a diagram of an example system 600. The substrate 610 is implanted into the dermal region 695 of the skin 605 which includes the epidermis 690 and subcutaneous fat layer 697 and an external reader 680 is positioned proximate to the substrate 610. It is noted that relative dimensions in FIG. 6A are not necessarily to scale, but have been rendered for purposes of explanation.

Figure 6B:
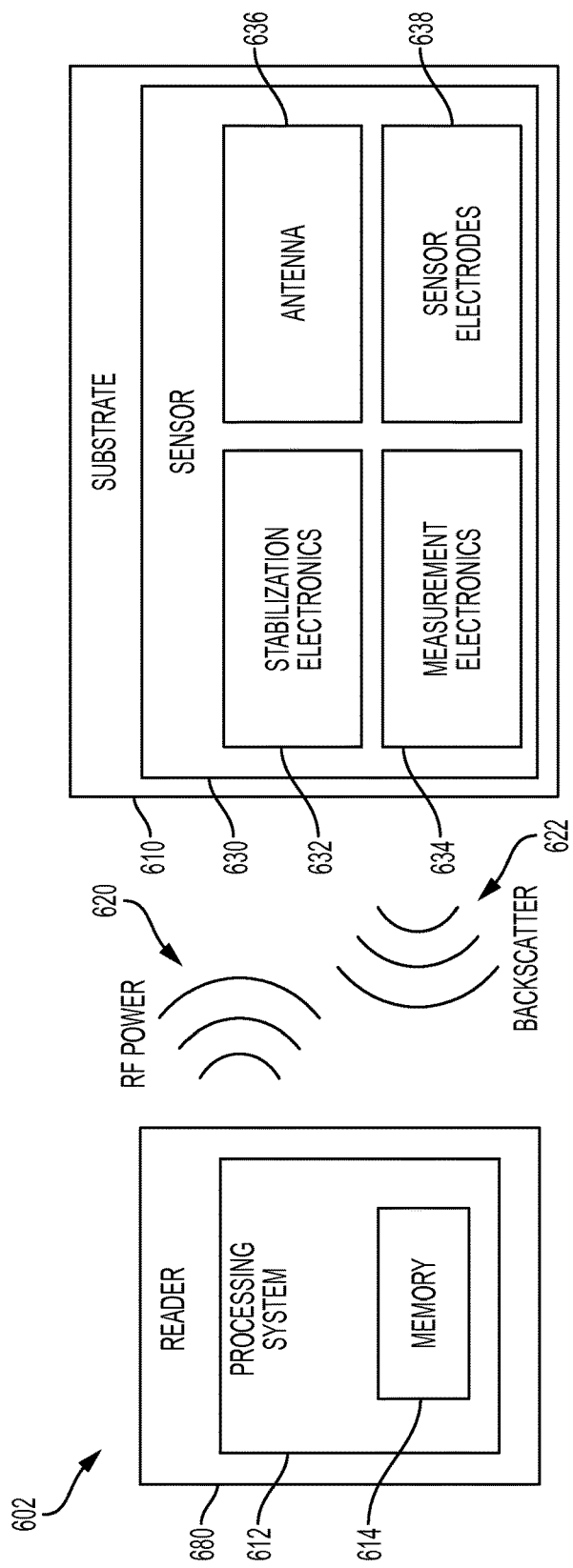
FIG. 6B is a block diagram of an implanted electrochemical sensor system operated by a reader device to obtain a series of amperometric current measurements over time, in accordance with an example embodiment.

In some embodiments, the substrate 610 may include an electrochemical sensor 630. FIG. 6B is a block diagram of implantable system described in connection with substrate 610 and reader 680 in FIG. 6A. System 602 includes a substrate 610 operated by a reader 680 to obtain one or more measurements related to an analyte in the interstitial fluid of the skin 605. An electrochemical sensor 630; e.g., an embodiment of bio-interactive electronics 660, can be included with substrate 610. As shown in FIG. 6A, substrate 610 is configured to be implanted under an external skin surface 605. The implanted electrochemical sensor can be operated to be transitioned into an active measurement mode in response to receiving a measurement signal from the reader 680.

The reader 680 includes a processing system 612, configured with memory 614. The processing system 612 can be a computing system that executes computer-readable instruction stored in the memory 614 to cause the reader 680/system 602 to obtain a time series of measurements by intermittently transmitting a measurement signal to substrate 610. In response to the measurement signal, one or more sensors of substrate 610; e.g., implantable electrochemical sensor 630, can take measurement(s), obtain results of the measurement(s), and communicate the results as shown in connection to reader 680 via backscatter 622. Reader 680 can provide power, such as RF power 620, to be harvested by the sensor 630. For example, impedance of an antenna of substrate 610 can be modulated in accordance with the sensor result such that the backscatter radiation 622 indicates the sensor results. Reader 680 can also use memory 614 to store indications of amperometric current measurements communicated by the implanted electrochemical sensor 630. The reader 680 can thus be operated to intermittently power the implanted electrochemical sensor 630 so as to obtain a time series of amperometric current measurements.

The implantable electrochemical sensor 630 can include stabilization electronics 632, measurement electronics 634, an antenna 636, and sensor electrodes 638. The stabilization electronics 632 can be configured to apply a stabilization voltage between the sensor electrodes 638 while the implanted electrochemical sensor 630 is operating in a standby (or stabilization) mode. The measurement electronics 634 are configured to measure the amperometric current through the working electrode of the sensor electrodes 638 and communicate the measured amperometric current through the antenna 636.

The implantable electrochemical sensor 630 can include energy harvesting systems for harvesting energy from incident radiation (and/or other sources) to generate bias voltage to apply across sensor electrodes during the standby mode. The implantable electrochemical sensor 630 can also be configured to generate power from incident radiation to power measurement and communication electronics in response to receiving a measurement signal indicating initiation of an active measurement mode. For example, measurement electronics 634 can be configured to harvest energy from incident radio frequency radiation via the antenna 636 and use the harvested energy to power the measurement and communication of the amperometric current. In another embodiment, viral-based piezoelectric energy generation system can be included in the substrate. See, Lee et al., Nature Nanotechnology, 2012, Vol. 7, pp. 351-356, DOI:10.1038/NNANO.2012.69, which is incorporated by reference in its entirety.

Figure 6C:
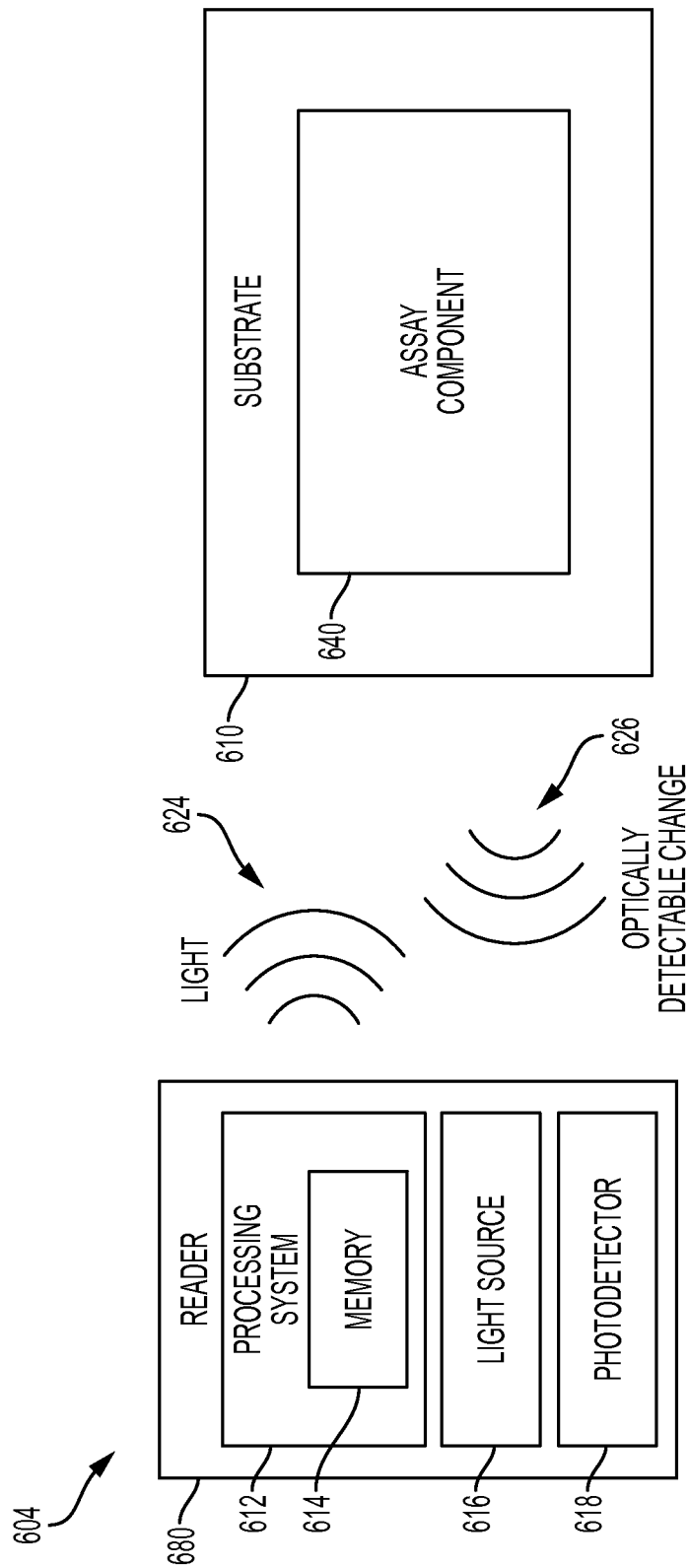
FIG. 6C is a block diagram of an implanted optical sensor system operated by a reader device capable of detecting an optically-detectable change in a substrate, in accordance with an example embodiment.

In other embodiments, the substrate 610 may include aptamer conjugates as an assay component 640. FIG. 6C is a block diagram of a system described in connection with substrate 610 and reader 680 in FIG. 6A. System 604 includes a substrate 610 operated by a reader 680 to obtain one or more measurements related to an analyte in the interstitial fluid of the skin. An assay component 640 configured to undergo an optically-detectable change 626 related to the analyte can be included with substrate 610. The optically-detectable change 626 may include a change in at least one of optical absorption, reflectivity, or fluorescence. As shown in FIG. 6A, substrate 610 is configured to be implanted beneath the external skin surface 405.

The implantable assay component 640 can be operated to a light source from the reader 680. The reader 680 may include a light source 616 configured to direct light 624 toward the assay component 640 of the substrate 610, and a photodetector 618 configured to detect light 626 from the assay component 640. For example, the substrate 610 may include aptamer conjugates as an assay component 640 that fluoresces upon interaction with an analyte. The reader 680 may be placed proximate to the substrate 610 so that the light source 616 may provide light 624 to the assay component 640. If the analyte is present, the assay component 640 may fluoresce, and the fluorescence 626 may be detected by the photo detector 618.

In other embodiments, sensor 630 can further include and/or be replaced by sensor(s) that measure light, heat/temperature (e.g., body temperature), blood pressure, air flow, altitude, and/or other characteristics than analyte concentration(s). In these other embodiments, sensor 630 can communicate data about the measured characteristics to reader 680 using backscatter communication 622.

V. Example Readers

The system includes a reader device ("reader"), that is configured to detect the interaction between the substrate and the analyte in the interstitial fluid. The reader can be a smart phone, digital assistant, or other portable computing device with wireless connectivity sufficient to communicate with the substrate. The function of the reader can be included in a "wearable device." The term "wearable device," as used in this disclosure, refers to any device that is capable of being worn at, on or in proximity to a body surface, such as a wrist, ankle, waist, chest, or other body part, e.g., an eye-glass frame, a head-mountable computer frame, a cap, a hat, part of a hat or cap (e.g., a hat band or bill of a baseball cap), a headphone headband, a watch, etc. In some examples, the reader is positioned proximate to the substrate only when a measurement is desired. In other examples, the reader is mounted proximate to the substrate so that the analyte-substrate interaction can be detected on demand or continuously without having to position the reader.

Figure 7A:
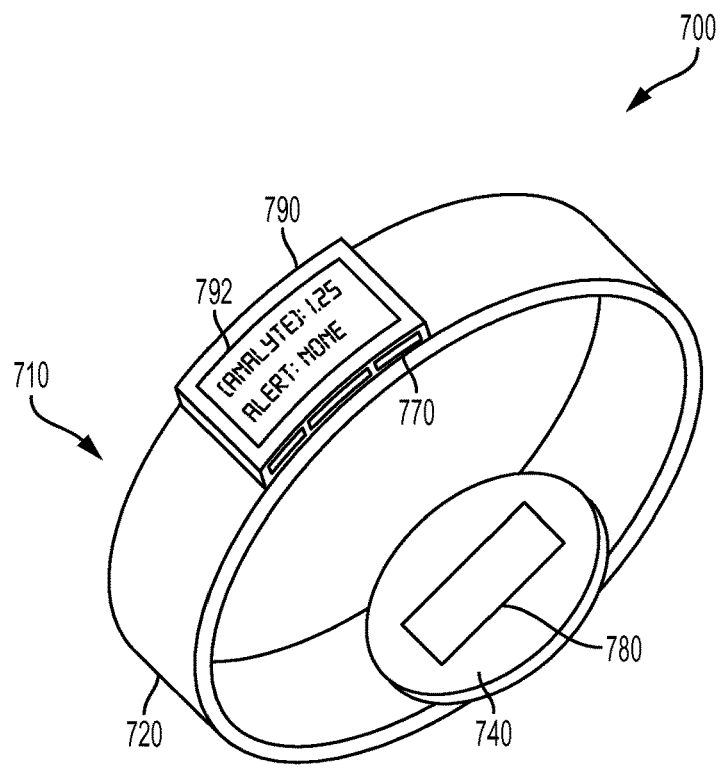
FIG. 7A is an example reader included in a wearable device in accordance with an example embodiment.
Figure 7B:
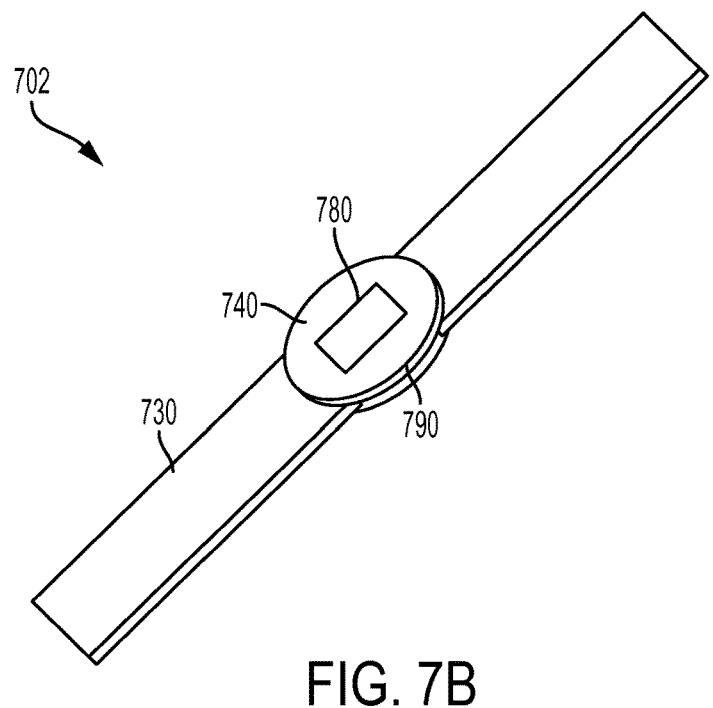
FIG. 7B is an example reader included in a wearable device in accordance with an example embodiment.

FIGS. 7A and 7B show example wearable devices 700 and 702. The device may be placed in close proximity to the implanted substrate. A mount 710, such as a belt, wristband, ankle band, etc. can be provided to mount the device at, on or in proximity to the body surface in close proximity to the implanted substrate. The mount 710 may prevent the wearable device from moving relative to the body to reduce measurement error and noise. In some embodiments, the wearable device is placed directly over the body surface above the implanted substrate. In one example, shown in FIG. 7A, the mount 710, may take the form of a strap or band 720 that can be worn around a part of the body. Further, the mount 710 may be an adhesive substrate for adhering the wearable device 700 to the body of a wearer.

A reader platform 740 is disposed on the mount 710 such that the reader platform 740 can be positioned proximate to the implanted substrate. The reader platform 740 may house the reader components 780 shown in FIG. 1. The wearable device 700 may also include a user interface 790 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 790 may include a display 792 where a visual indication of the alert or recommendation may be displayed. The display 792 may further be configured to provide an indication of the measured physiological parameters, for instance, the concentration of a measured analyte.

In another embodiment, as shown in FIG. 7B, the reader platform 740 may be positioned on the back side of the user interface 790.

In some embodiments, a reader can power a sensor in the substrate using a low-power transmission; e.g., a transmission of 1 watt or less of power. In these embodiments, the reader can be within a predetermined distance; e.g., 1 foot, 40 cm, of the substrate.

After receiving analyte-related data from the substrate, the reader can utilize the data; e.g., process, present, store, communicate, etc. For example, the reader can process the analyte-related data to generate an analyte concentration, and the display device can present the analyte concentration to the user.

In some embodiments, the reader may evaluate the analyte-related data and display a visual indication of an alert or recommendation and/or an indication of the measured physiological parameters. For example, the reader may compare an analyte concentration to a low- and/or high-analyte threshold(s) to determine, respectively, whether the analyte concentration is too high or low for the wearer of the system. If the blood-glucose data is too high or low for wearer, the display can alert wearer, attempt to contact another person or entity to help the wearer, and/or perform some other action.

Further, the user interface 790 may include one or more buttons 770 for accepting inputs from the wearer. For example, as shown in FIG. 7A, the buttons 770 for accepting inputs from the wearer. The buttons 770 may be configured to change the text or other information visible on the display 792. The buttons 770 may also be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

VII. Example Operations

In some embodiments, the present disclosure provides a method for operating a system including a substrate and a reader to measure an analyte concentration of an interstitial fluid in the skin. The method may include receiving, by a substrate, a signal from a reader device, a signal from a reader device, wherein the substrate includes a sensor comprising aptamer conjugates and is implanted into the skin; performing, by the sensor, in response to the signal, a measurement related to an analyte in the interstitial fluid; and communicating, by the substrate, data indicative of the measurement to the reader device.

In some embodiments, the substrate includes an antenna, and the signal includes a radio frequency (RF) signal.

In some embodiments, the signal is an optical signal and the data indicative of the measure comprising at least one of optical absorption, reflectivity, or fluorescence.

In another embodiment, the method may further include:
transmitting, by a reader device, a signal to a substrate implanted in the skin, the substrate comprising a sensor, the sensor comprising aptamer conjugates, wherein the sensor is configured to obtain one or more measurements related to an analyte in interstitial fluid; and
receiving, by the reader device, a responsive signal from the substrate, wherein the responsive signal may indicate the one or more measurements related to the analyte in the interstitial fluid, from which the concentration of an analyte in the interstitial fluid may be determined.

In some embodiments, the substrate may include an antenna and a sensor. The signal and the responsive signal may be radio frequency (RF) signals. In some examples, the responsive signal includes data indicative of one or more measurements related to the analyte obtained by the sensor. In some embodiments, the responsive signal may indicate the concentration of one or more analytes in interstitial fluid.

In some embodiments, the signal and the responsive signal may be optical signals. The substrate may include a sensor comprising aptamer conjugates which is configured to undergo an optically-detectable change related to the analyte. In some examples, the optically-detectable change may involve a change in at least one of optical absorption, reflectivity, or fluorescence. In some embodiments the responsive signal indicates the presence or absence of an analyte and/or amount, level or concentration of the analyte in interstitial fluid. The responsive signal that is generated is due to the presence of the analyte in the interstitial fluid of the subject and these interstitial fluid analyte levels are related to the blood analyte levels in the subject. In general, the interstitial fluid analyte levels are directly related to the blood analyte levels of the subject. Thus, in one embodiment, the interstitial fluid analyte levels serve as a surrogate for the blood analyte levels of the subject. In another embodiment, the interstitial fluid analyte levels may be correlated to the blood analyte levels.

Figure 8:
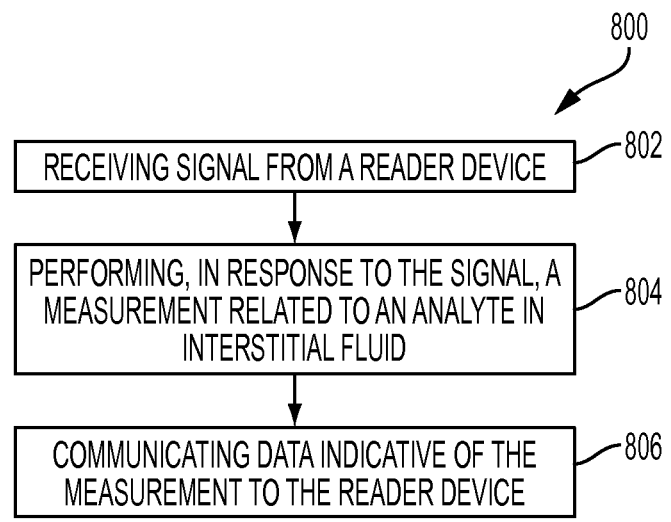
FIG. 8 is a flowchart of an example method for operating a system with an implanted substrate to measure an analyte in interstitial fluid in the skin.

FIG. 8 is a flowchart of a method 800 for operating a system including a substrate implanted beneath the skin surface to measure an analyte in an interstitial fluid in the skin. The method includes receiving a signal from a reader device (802). In some embodiments, the substrate may include an antenna and the signal may be electromagnetic radiation, such as a radio frequency (RF) signal. In other embodiments, the signal may be optical, such as visible light. The method further includes performing, in response to the signal, a measurement related to an analyte in the interstitial fluid in the skin (804). For example, when the substrate includes an optical sensor selectively sensitive to an analyte, the measurement may be the concentration of the analyte. In other embodiments, where the substrate includes a component configured to undergo an optically-detectable change related to an analyte, the measurement may be the presence, absence or concentration of the analyte. The method also includes communicating data indicative of the measurement to the reader device (806). For example, when the substrate includes an antenna, the communicating may be the transmitting of a radio frequency (RF) via the antenna. In other examples, the communicating may be achieved by an optical signal from the substrate, such as a change in optical absorption, reflectivity, or fluorescence.

Figure 9:
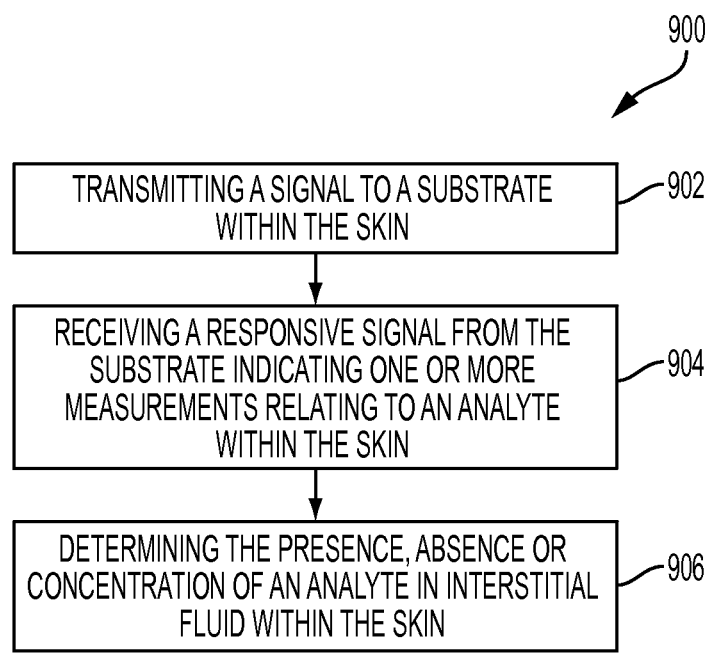
FIG. 9 is a flowchart of an example method for operating a system with an external reader and an implanted substrate to measure an analyte in an interstitial fluid in the skin.

FIG. 9 is a flowchart of a method 900 for operating a system including a reader and a substrate implanted in the skin to measure an analyte in the interstitial fluid in the skin. The method includes transmitting a signal to a substrate on an external skin surface (902). In some examples, the substrate includes an antenna and the signal is a radio frequency (RF) signal. In other embodiments, the signal may be optical, such as visible light. The method further includes receiving a responsive signal from the substrate (904). The responsive signal may indicate one or more measurements related to an analyte in the interstitial fluid in the skin. For example, when the substrate includes an antenna, the responsive signal may be a radio frequency (RF) signal. In other examples, the responsive signal may be an optical signal, such as a change in optical absorption, reflectivity, or fluorescence. In some embodiments, the method may further include determining the presence, absence or concentration of an analyte in the interstitial fluid in the skin (906). In embodiments where the substrate includes an electrochemical sensor selectively sensitive to an analyte, the concentration of the analyte may be determined. In embodiments where the substrate includes a component configured to undergo an optically-detectable change related to an analyte, the presence, absence or concentration of the analyte, may be determined.

VIII. Conclusion

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying figures. In the figures, similar symbols typically identify similar components, unless context dictates otherwise. The example embodiments described herein and in the figures are not meant to be limiting. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the ladder diagrams, scenarios, and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the ladder diagrams, scenarios, and flow charts discussed herein, and these ladder diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include non-transitory computer readable media such as computer-readable media that stores data for short periods of time like register memory, processor cache, and random access memory (RAM). The computer readable media may also include non-transitory computer readable media that stores program code and/or data for longer periods of time, such as secondary or persistent long term storage, like read only memory (ROM), optical or magnetic disks, compact-disc read only memory (CD-ROM), for example. The computer readable media may also be any other volatile or non-volatile storage systems. A computer readable medium may be considered a computer readable storage medium, for example, or a tangible storage device.

Moreover, a block that represents one or more information transmissions may correspond to information transmissions between software and/or hardware modules in the same physical device. However, other information transmissions may be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

It will be readily understood that the aspects of the present disclosure, as generally described herein, and illustrated in the figures, can be arranged, substituted, combined, separated, and designed in a wide variety of different configurations, all of which are explicitly contemplated herein. While various aspects and embodiments have been disclosed herein, other aspects and embodiments will be apparent to those skilled in the art.

Example methods and systems are described above. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Reference is made herein to the accompanying figures, which form a part thereof. In the figures, similar symbols typically identify similar components, unless context dictates otherwise. Other embodiments may be utilized, and other changes may be made, without departing from the spirit or scope of the subject matter presented herein. The various aspects and embodiments disclosed herein are for purposes of illustration and are not intended to be limiting, with the true scope and spirit being indicated by the following claims.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The invention claimed is:

1. A system, comprising:
a substrate comprising
a polymeric material formed to be implanted into skin,
a mounting platform embedded in the polymeric material, wherein the mounting platform and the polymeric material are composed of different materials,
bio-interactive electronics mounted onto a surface of the mounting platform, the bio-interactive electronics comprising a sensitizing layer and a sensor associated with the sensitizing layer, the sensor comprising aptamer conjugates, wherein the sensor is configured to obtain one or more measurements related to at least one analyte in interstitial fluid; and
a reader device, wherein the reader device is configured to detect the analyte in interstitial fluid via interaction with the substrate.

2. The system of claim 1, wherein the aptamer conjugate comprises a labeled aptamer conjugated to a polymer.

3. The system of claim 2, wherein the labeled aptamer possesses or comes to possess a detectable signal.

4. The system of claim 1, wherein the sensor is configured to obtain one or more measurements related to multiple analytes.

5. The system of claim 1, wherein the substrate further comprises an antenna, and wherein the reader device is configured to detect the analyte based on data communicated via the antenna.

6. The system of claim 5, wherein the data communicated via the antenna is indicative of the one or more measurements.

7. The system of claim 6, wherein the sensor is an electrochemical sensor comprising a working electrode and a reference electrode.

8. The system of claim 1, wherein the substrate comprises a component configured to undergo an optically-detectable change related to the analyte, wherein the optically-detectable change comprises a change in at least one of optical absorption, reflectivity, or fluorescence.

9. The system of claim 8, wherein the reader device is configured to detect the optically-detectable change.

10. The system of claim 9, wherein the optically-detectable change is optical absorption, reflectivity, or fluorescence.

11. The system of claim 9, wherein the reader device comprises:
a light source configured to direct light toward the substrate; and
a photodetector configured to detect light from the substrate.

12. The system of claim 1, wherein
the at least one analyte comprises an ion, and
the sensitizing layer further comprises an ionophore.

13. The system of claim 1, wherein
the reader further comprises a first antenna; and
the substrate further comprises a second antenna, wherein the reader is configured to provide radio frequency (RF) power to the substrate via the first antenna, the sensor is configured to harvest the RF power, measure an analyte concentration level, and communicate a sensor reading back to the reader via the second antenna.

14. The system of claim 1, wherein the reader is a wearable device.

15. The system according to claim 1, wherein the substrate further includes a channel for allowing the bio-active electronics to receive interstitial fluid.

16. The system according to claim 1, wherein the sensitizing layer comprises a polymer that is permeable to the at least one analyte.

17. A method, comprising:
receiving, by a substrate, a signal from a reader device, wherein the substrate comprises a polymeric material formed to be implanted into skin, a mounting platform embedded in the polymeric material, wherein the mounting platform and the polymeric material are composed of different materials, bio-interactive electronics mounted onto a surface of the mounting platform, the bio-interactive electronics comprising a sensitizing layer and a sensor associated with the sensitizing layer, the sensor comprising aptamer conjugates, and wherein the substrate is implanted into skin;
performing, by the sensor, in response to the signal, a measurement related to at least one analyte in interstitial fluid; and
communicating, by the substrate, data indicative of the measurement to the reader device.

18. The method of claim 17, wherein the signal is a radio frequency (RF) signal, and wherein the substrate comprises an antenna.

19. The method of claim 17, wherein the signal is an optical signal, and wherein the data indicative of the measurement comprises at least one of optical absorption, reflectivity, or fluorescence.

20. A method, comprising:
transmitting, by a reader device, a signal to a substrate implanted into skin, the substrate comprising a polymeric material formed to be implanted into skin, a mounting platform embedded in the polymeric material, wherein the mounting platform and the polymeric material are composed of different materials, bio-interactive electronics mounted onto a surface of the mounting platform, the bio-interactive electronics comprising a sensitizing layer and a sensor associated with the sensitizing layer, the sensor comprising aptamer conjugates, wherein the sensor is configured to obtain one or more measurements related to at least one analyte in interstitial fluid; and
receiving, by the reader device, a responsive signal from the substrate, wherein the responsive signal indicates the one or more measurements related to the analyte in the interstitial fluid.

21. The method of claim 20, wherein the substrate further comprises an antenna, wherein the signal and the responsive signal are radio frequency (RF) signals, and wherein the responsive signal comprises data indicative of the one or more measurements related to the analyte obtained by the sensor.

22. The method of claim 20, wherein the signal and the responsive signal are optical signals, wherein the substrate comprises a component configured to undergo an optically-detectable change related to the analyte, wherein the optically-detectable change comprises a change in at least one of optical absorption, reflectivity, or fluorescence, and wherein the responsive signal indicates the concentration of an analyte in interstitial fluid.

* * * * *